(12) United States Patent
Mellman et al.

(10) Patent No.: US 10,265,407 B2
(45) Date of Patent: *Apr. 23, 2019

(54) MODULAR NANODEVICES FOR SMART ADAPTABLE VACCINES

(71) Applicant: Yale University, New Haven, CT (US)

(72) Inventors: Ira S. Mellman, San Francisco, CA (US); Tarek M. Fahmy, New Haven, CT (US); William Mark Saltzman, New Haven, CT (US); Michael J. Caplan, Woodbridge, CT (US)

(73) Assignee: Yale University, New Haven, CT (US)

( * ) Notice: Subject to any disclaimer, the term of this patent is extended or adjusted under 35 U.S.C. 154(b) by 450 days.

This patent is subject to a terminal disclaimer.

(21) Appl. No.: 14/537,541

(22) Filed: Nov. 10, 2014

(65) Prior Publication Data

US 2015/0125384 A1 May 7, 2015

Related U.S. Application Data

(63) Continuation-in-part of application No. 12/527,143, filed as application No. PCT/US2008/054086 on Feb. 15, 2008, now Pat. No. 8,889,117.

(Continued)

(51) Int. Cl.
| | | |
|---|---|---|
| *A61K 9/14* | (2006.01) | |
| *A61K 9/51* | (2006.01) | |
| *A61K 47/50* | (2017.01) | |
| *A61K 47/60* | (2017.01) | |
| *A61K 47/66* | (2017.01) | |
| *A61K 39/02* | (2006.01) | |
| *A61K 39/12* | (2006.01) | |
| *A61K 39/35* | (2006.01) | |
| *A61K 39/395* | (2006.01) | |
| *C07K 14/47* | (2006.01) | |
| *C07K 14/705* | (2006.01) | |
| *C07K 16/18* | (2006.01) | |
| *C07K 16/28* | (2006.01) | |
| *C07K 16/30* | (2006.01) | |
| *A61K 47/48* | (2006.01) | |

(Continued)

(52) U.S. Cl.
CPC .......... *A61K 47/48915* (2013.01); *A61K 9/14* (2013.01); *A61K 9/5084* (2013.01); *A61K 9/51* (2013.01); *A61K 9/5153* (2013.01); *A61K 9/5161* (2013.01); *A61K 39/001* (2013.01); *A61K 39/0005* (2013.01); *A61K 39/0011* (2013.01); *A61K 39/02* (2013.01); *A61K 39/12* (2013.01); *A61K 39/145* (2013.01); *A61K 39/35* (2013.01); *A61K 39/385* (2013.01); *A61K 39/39* (2013.01); *A61K 47/58* (2017.08); *A61K 47/62* (2017.08); *A61K 47/6849* (2017.08); *A61K 47/6937* (2017.08); *C07K 16/18* (2013.01); *A61K 9/141* (2013.01); *A61K 39/3955* (2013.01); *A61K 2039/55516* (2013.01); *A61K 2039/57* (2013.01); *A61K 2039/6093* (2013.01); *A61K 2039/70* (2013.01); *C07K 14/47* (2013.01); *C07K 14/705* (2013.01); *C07K 16/28* (2013.01); *C07K 16/2851* (2013.01); *C07K 16/30* (2013.01); *C12N 2710/16134* (2013.01); *C12N 2710/16234* (2013.01); *C12N 2760/16134* (2013.01)

(58) Field of Classification Search
CPC ........ A61K 47/48884; A61K 47/48953; A61K 47/48338; A61K 2039/505; A61K 2039/55555; A61K 47/48561; A61K 39/0002; A61K 39/0003; A61K 39/0004; A61K 39/002; A61K 39/0008; A61K 39/12; A61K 47/48892; A61K 9/14; A61K 9/51; A61K 39/38; A61K 39/3955; A61K 39/0005; A61K 39/0011; A61K 39/35; A61K 39/02; C07K 16/28; C07K 14/47; C07K 14/705; C07K 16/3007
See application file for complete search history.

(56) References Cited

U.S. PATENT DOCUMENTS

| 4,191,743 A | 3/1980 | Klemm |
|---|---|---|
| 4,316,885 A | 2/1982 | Rakhit |

(Continued)

FOREIGN PATENT DOCUMENTS

| WO | 9205179 | 2/1992 |
|---|---|---|
| WO | 9503357 | 2/1995 |

(Continued)

OTHER PUBLICATIONS

Almeida et al. Solid lipid nanoparticles as a drug delivery system for peptides and proteins. Adv Drug Delivery Rev 59: 478-490, 2007.*

(Continued)

*Primary Examiner* — Bridget E Bunner
(74) *Attorney, Agent, or Firm* — Pabst Patent Group LLP

(57) ABSTRACT

Modular nanoparticle vaccine compositions and methods of making and using the same have been developed. Modular nanoparticle vaccine compositions comprise an antigen encapsulated in a polymeric particle and adaptor elements which modularly couple functional elements to the particle. The modular design of these vaccine compositions, which involves flexible addition and subtraction of antigen, adjuvant, immune potentiators, molecular recognition and transport mediation elements, as well as intracellular uptake mediators, allows for exquisite control over variables that are important in optimizing an effective vaccine delivery system.

28 Claims, 11 Drawing Sheets

Specification includes a Sequence Listing.

Related U.S. Application Data

(60) Provisional application No. 60/890,133, filed on Feb. 15, 2007, provisional application No. 61/000,016, filed on Oct. 23, 2007.

(51) Int. Cl.

| | | |
|---|---|---|
| A61K 39/39 | (2006.01) | |
| A61K 39/00 | (2006.01) | |
| A61K 39/145 | (2006.01) | |
| A61K 9/50 | (2006.01) | |
| A61K 39/385 | (2006.01) | |
| A61K 47/58 | (2017.01) | |
| A61K 47/62 | (2017.01) | |
| A61K 47/68 | (2017.01) | |
| A61K 47/69 | (2017.01) | |

(56) References Cited

U.S. PATENT DOCUMENTS

| | | |
|---|---|---|
| 4,384,996 A | 5/1983 | Bollinger |
| 4,650,803 A | 3/1987 | Stella |
| 4,798,823 A | 1/1989 | Witzel |
| 4,894,366 A | 1/1990 | Okuhara |
| 4,929,611 A | 5/1990 | Okuhara |
| 4,956,352 A | 9/1990 | Okuhara |
| 5,100,883 A | 3/1992 | Schiehser |
| 5,118,678 A | 6/1992 | Kao |
| 5,120,725 A | 6/1992 | Kao |
| 5,120,727 A | 6/1992 | Kao |
| 5,120,842 A | 6/1992 | Failli |
| 5,122,511 A | 6/1992 | Patchett |
| 5,143,918 A | 9/1992 | Bochis |
| 5,151,413 A | 9/1992 | Caufield |
| 5,162,334 A | 11/1992 | Goulet |
| 5,169,851 A | 12/1992 | Hughes |
| 5,189,042 A | 2/1993 | Goulet |
| 5,202,332 A | 4/1993 | Hughes |
| 5,208,228 A | 5/1993 | Ok |
| 5,227,467 A | 7/1993 | Durette |
| 5,250,678 A | 10/1993 | Goulet |
| 5,254,562 A | 10/1993 | Okuhara |
| 5,258,389 A | 11/1993 | Goulet |
| 5,262,533 A | 11/1993 | Sinclair |
| 5,284,826 A | 2/1994 | Eberle |
| 5,284,840 A | 2/1994 | Rupprecht |
| 5,504,091 A | 4/1996 | Kimber |
| 5,532,248 A | 7/1996 | Goulet |
| 5,543,158 A | 8/1996 | Gref |
| 5,693,648 A | 12/1997 | Goulet |
| 5,709,797 A | 1/1998 | Bocchiola |
| 5,962,566 A | 10/1999 | Grandfils |
| 5,972,366 A | 10/1999 | Haynes |
| 6,136,357 A | 10/2000 | Dietl |
| 6,503,921 B2 | 1/2003 | Naicker |
| 6,544,543 B1 | 4/2003 | Mandrusov |
| 6,551,990 B2 | 4/2003 | Giachelli |
| 6,676,963 B1 | 1/2004 | Lanza |
| 6,793,938 B2 | 9/2004 | Sankaram |
| 7,534,448 B2 | 5/2009 | Saltzman |
| 7,534,449 B2 | 5/2009 | Saltzman |
| 7,550,154 B2 | 6/2009 | Saltzman |
| 8,889,117 B2 | 11/2014 | Mellman |
| 2001/0031262 A1 | 10/2001 | Caplan |
| 2002/0044959 A1 | 4/2002 | Goetz |
| 2002/0132763 A1 | 9/2002 | Salvaraj |
| 2002/0155607 A1 | 10/2002 | Boutin |
| 2003/0235619 A1 | 12/2003 | Allen |
| 2004/0022840 A1 | 2/2004 | Nagy |
| 2006/0002852 A1 | 1/2006 | Saltzman |
| 2006/0002971 A1 | 1/2006 | Saltzman |
| 2006/0051426 A1 | 3/2006 | Golomb |
| 2010/0284965 A1 | 11/2010 | Fahmy |

FOREIGN PATENT DOCUMENTS

| | | |
|---|---|---|
| WO | 9620698 | 7/1996 |
| WO | 9952550 | 10/1999 |
| WO | 00029043 | 5/2000 |
| WO | 02067849 | 9/2002 |
| WO | 020764410 | 10/2002 |
| WO | 03087021 | 10/2003 |
| WO | 04071493 | 8/2004 |
| WO | 06037979 | 4/2006 |
| WO | 06050170 | 5/2006 |
| WO | 2008115641 | 9/2008 |
| WO | 08109347 | 9/2009 |
| WO | 2005021730 | 3/2010 |

OTHER PUBLICATIONS

Newman et al. Uptake of poly(D,L-lactic-co-glycolic acid) microspheres by antigen-presenting cells in vivo. J Biomed Mater Res 60: 480-486, 2002.*

Solbrig et al. Polymer nanoparticles for immunotherapy from encapsulated tumor-associated antigens and whole tumor cells. Mol Pharmaceut 4(1): 47-57, 2007.*

Butler et al. Altered expression and endocytic funcction of CD205 in human dendritic cells, and detection of a CD205-DCL-1 fusion protein upon dendritic cell maturation. Immunology 120: 362-371, 2006.*

Demento et al. Pathogen-associated molecular patterns on biomaterials: a paradigm for engineering new vaccines. Trends Biotechnol 29(6): 294-306, 2011.*

Tacken et al. Targeting antigens to dendritic cell in vivo. Immunobiol 211: 599-608, 2006.*

Aguado, et al., "Controlled-release vaccinesbiodegradable polylactide/polyglycolide (PL/PG) microspheres as antigen vehicles," Immunobiology, 184 (2-3): 113-25 (1992).

Anderson and Shive, et al., "Biodegradation and biocompatibility of PLA and PLGA microspheres", Adv Drug Deliv Rev,#s(28#1):5-24 (1997).

Blanchette, et al., "Cellular evaluation of oral chemotherapy carriers," J. Biomed. Mater. Res. A, 72(4):381-8 (2005).

Blanchette, et al., "Oral chemotherapeutic delivery: design and cellular response," Ann. Biomed. Eng., 33(2):142-9 (2005).

Bonifaz, et al., "Efficient targeting of protein antigen to the dendritic cell receptor DEC-205 in the steady state leads to antigen presentation on major histocompatibility complex class I products and peripheral CD8+ T cell tolerance," J. Exp. Med., 196(12):1627-38, (2002).

Bonifaz, et al., In vivo targeting of antigens to maturing dendritic cells via the DEC-205 receptor improves T cell vaccination, J. Exp., Med., 199(6):815-24 (2004).

Bourges, et al., "Ocular drug delivery targeting the retina and retinal pigment epithelium using polylactide nanoparticles", Invest Ophthalmol Vis Sci, 44:3562-3569 (2003).

Bourla, et al., "Age-related macular degeneration: a practical approach to a challenging disease", J. Am. Geriatr. Soc, 54(7): 1130-5 (2006).

Bramwell, et al., "Particulate delivery systems for biodefense subunit vaccines," Adv. Drug Deliv. Rev. 57(9): 1247-65 (2005).

Bramwell, etal., "The rational design of vaccines," Drug Discovery Today, 10 (22): 1527-34 (2005).

Brigger, et al., "Nanoparticles in cancer therapy and diagnosis", Adv Drug Deliv Rev, 54:631-651 (2002).

Brunner, et al., "pH and osmotic pressure inside biodegradable microspheres during erosion", Pharm Res, 16(6):847-53(1999).

Calvo, et al., "Chitosan and chitosan/ethylene oxide-propylene oxide block copolymer nanoparticles as novel carriers for proteins and vaccines." Pharm. Res., 14(10):1431-36 (1997).

Cannizzaro, et al., "A novel biotinylated degradable polymer for cell-interactive applications", Biotech Bioeng., 58(5):529-35 (1998).

Cao, et al., "Production and surface modification of polylactide-based polymeric scaffolds for soft-tissue engineering", Methods Mol Biol, 238:87-112 (2004).

(56) References Cited

OTHER PUBLICATIONS

Caponetti, et al., "Microparticles of novel branched copolymers of lactic acid and amino acids: preparation and characterization", J Pharm Sci, 88(1):136-41 (1999).
Challacombe, et al., "Enhanced secretory IgA and systemic IgG antibody responses after oral immunization with biodegradable microparticles containing antigen," Immunology, 76(1):164-8 (1992).
Cho, et al., "Receptor-mediated delivery of all trans-retinoic acid to hepatocyte using poly(L-lactic acid) nanoparticles coated with galactose-carrying polystyrene", J Control Release, 77:7-15 (2001).
Cremaschi, et al., "Different kinds of polypeptides and polypeptide-coated nanoparticles are accepted by the selective transcytosis show in the rabbit nasal mucosa," Biochim. Biophys. Acta, 1416(1-2):31-8 (1999).
Cremaschi, et al., "Further analysis of transcytosis of free polypeptides and polypeptide-coated nanobeads in rabbit nasal mucosa," J. Appl. Physiol., 91 (1):211-7 (2001).
Croll, "Controllable surface modification of poly(lactic-co-glycolic acid) (PLGA) by hydrolysis or aminolysis I: physical, chemical, and theoretical aspects", Biomacromolecules, 5(2):463-73 (2004).
Cui, et al., "Intradermal immunization with novel plasmid DNA-coated nanoparticles via a needle-free injection device," J. Biotechnology, 102(2): 105-15 (2003).
De Kozak, "Intraocular injection of tamoxifen-loaded nanoparticles: a new treatment of experimental autoimmune uveoretinitis", Eur J Immunol, 34: 3702-3712 (2004).
Dev, et al., "Kinetics of drug delivery to the arterial wall via polyurethane-coated removable nitinol stent: comparative study of two drugs", Cathet. Cardiovasc. Diagn., 34(3):272-278 (1995).
Dev, et al., "Sustained local drug delivery to the arterial wall via biodegradable microspheres", Cathet. Cardiovasc. D/agn.,41(3):324-332(1997).
Edelman, et al., "Effect of controlled adventitial heparin delivery on smooth muscle cell proliferation following endothelial injury", Proc. Natl. Acad. Sci. U.S.A., 87(10):3773-3777 (1990).
Edwards, et al., "Complement Factor H Polymorphism and Age-Related Macular Degeneration", Science, 308(5720):421-4 (2005).
Elamanchili, et al., "Characterization of poly(D,L-lactic-co-glycolic acid) based nanoparticulate system for enhanced delivery of antigens to dendritic cells", Vaccine, 22:2406-2412 (2004).
Eldridge, et al., "Biodegradable and biocompatible poly(DL-lactide-co-glycolide) microspheres as an adjuvant for staphylococcal enterotoxin-B toxoid which enhances the level of toxic-neutralizing antibodies," Infection and immunity, 59(9):2978-2986(1991).
Eldridge, et al., "Biodegradable microspheres-Vaccine delivery system for oral immunization," Current Topics in Microbiology and Immunology, 146:59-66 (1989).
Eldridge, et al., "Controlled vaccine release in the gut-associated lymphoid tissues.1. Orally-administered biodegradable microspheres target the Peyers patches," J. Control. Release, 11 (1-3):205-214 (1990).
Eliaz and Szoka, "Liposome-encapsulated doxorubicin targeted to CD44: a strategy to kill CD44-overexpressing tumor cells", Cancer Res, 61: 2592-2601 (2001).
Eniola, et al., "Artificial polymeric cells for targeted drug delivery", J Control Release 87(1-3):15-22 (2003).
Evora, et al., "Relating the phagocytosis of microparticles by alveolar macrophages to surface chemistry: the effect of 1,2-dipalmitoylphosphatidylcholine", J Control Release 51 (2-3): 143-52 (1998).
Fahmy, "Increased TCR avidity after T cell activation: a mechanism for sensing low-density antigen", Immunity, 14:135-43(2001).
Fahmy, et al., "Surface modification of biodegradable polyesters with fatty acid conjugates for improved drug targeting," Biomatehals, 26(28):5727-36 (2005).
Fahmy, et al., "Targeted for drug delivery," Materials Today, 8(8, Supplement 1):18-26 (2005).
Faraasen, et al., "Ligand-specific targeting of microspheres to phagocytes by surface modification with poly(L-lysine)-grafted polyethylene glycol) conjugate", Pharm Res, 20 (2):237-46 (2003).

Friede, et al., "Need for new vaccine formulations and potential of particulate antigen and DNA delivery systems," Adv. DrugDeliv. Rev., 57(3):325-31 (2005).
Garcia-Garcia, et al., "Drug-eluting stents", Arch Cardiol Mex, 76(3):297-319 (2006) (abstract).
Gref, "'Stealth' corona-core nanoparticles surface modified by polyethylene glycol (PEG): influences of the corona (PEG chain length and surface density) and of the core composition on phagocytic uptake and plasma protein adsorption", Colloids and Surfaces B: Biointerfaces, 18(3-4): 301-313 (2000).
Gref, "Surface-engineered nanoparticles for multiple ligand coupling", Biomatehals, 24(24): 4529-4537 (2003).
Gupta, et al., "Adjuvants for human vaccinescurrent status, problems, and future prospects," Vaccine, 13(14):1263-76 (1995).
Gupta, et al., "Poly(lactide-co-glycolide) microparticles for the development of single-dose controlled release vaccines," Adv. Drug Deliv. Rev., 32(3):225-246 (1998).
Guzman, et al., "Local intraluminal infusion of biodegradable polymeric nanoparticles. A novel approach for prolonged drug delivery after balloon angioplasty", Circulation, 94:1441-1448 (1996).
Haines, et al., "Complement factor H variant increases the risk of age-related macular degeneation", Science, 308(5720):419-21 (2005).
Hallahan, et al., "Integrin-mediated targeting of drug delivery to irradiated tumor blood vessels", Cancer Cell, 3:63-74 (2003).
Hammer, et al., "Synthetic cells-self-assembling polymer membranes and bioadhesive colloids", Annu Rev Mater Res, 31:387-40 (2001).
Hariharan, et al., "Improved graft survival after renal transplantation in the United States, 1988 to 1996", N. Engl. J. Med.,342(9):605-612(2000).
Hattori, et al., "Enhanced in vitro DNA transfection eflicientcy by novel folate-linked nanoparticles in human prostate cancer and oral cancer" J Control Release 97:173-183(2004).
Hawiger, et al., "Dendritic cells: specialized and regulated antigen processing machines," J. Exp. Med., 194(6):769-79 (2001).
Hood, et al., "Tumor regression by targeted gene delivery to the neovasculature", Science, 296(5577):2404-2407 (2002).
Huang, "Monoclonal antibody covalently coupled with fatty acid. A reagent for in vitro liposome targeting", J Biol Chem, 255(17):8015-8 (1980).
Humphrey, "The effect of intramural delivery of polymeric nanoparticles loaded with the antiproliferative 2-aminochromone U-86983 on neointimal hyperplasia development in balloon injured porcine coronary arteries.", Adv. Drug Del. Rev., 24:87-108 (1997).
Italia, et al., "Disease, destination, dose and delivery aspects of ciclosporin: the state of the art", Drug Discov. Today, 11(17-18):846-854 (2006).
Jain, "The manufacturing techniques of various drug loaded biodegradable poly (lactide-co-glycolide) (PLGA) devices", Biomatehals, 21(23):2475-90 (2000).
Jansen, et al., "Encapsulation of Guest Molecules into a Dendritic Box", Science, 266(5188): 1226-1229 (1994).
Jansen, et al., "The Dendritic Box: Shape-Selective Liberation of shell deprotection Encapsulated Guests", J Am Chem Soc, 117:4417-4418(1995).
Jiang, et al., "Biodegradable poly(lactic-co-glycolic acid) microparticles for injectable delivery of vaccine antigens," Adv. Drug Deliv. Rev., 57(3):391-410 (2005).
Johansen, et al, "Revisiting PLA/PLGA microspheres: an analysis of their potential in parenteral vaccination", Eur J Pharm Biopharm, 50(1):129-46 (2000).
Keegan, et al., "Biodegradable Microspheres with Enhanced Capacity for Covalently Bound Surface Ligands" Macromolecules, 37:9979-84 (2004).
Keegan, et al., "Biomimetic design in microparticulate vaccines," Biomatehals, 24(24):4435-43 (2003).
Klein, et al., "Complement factor H polymorphism in age-related macular degeneration", Science, 308(5720):385-9 (2005).
Kobayashi, "Evaluation of the in vivo biodistribution of indium-111 and yttrium-88 labeled dendrimer-1B4M-DTPA and its conjugation with anti-Tac monoclonal antibody", Bioconjug Chem, 10:103-11 (1999).

(56) References Cited

OTHER PUBLICATIONS

Kobayashi, et al., "Dendrimer-based Macromolecular MRI Contrast Agents: Characteristics and Application", Mol Imaging, 2:1-10 (2003).
Kohn, et al., "Single-step immunization using a controlled release, biodegradable polymer with sustained adjuvant activity," J. Immunol. Methods, 95(1):31-8 (1986).
Kompella, et al., "Subconjunctival nano- and microparticles sustain retinal delivery of budesonide, a corticosteroid capable of inhibiting VEGF expression", Invest Ophthalmol Vis Sci, 44(3):1192-201 (2003).
Kono, et al., Abstracts of Papers of the American Chemical Society, 221:1) 377-11377 (2001).
Kwon, et al., "Enhanced antigen presentation and immunostimulation of dendritic cells using acid-degradable cationic nanoparticles," J. Control Release, 105(3):119-212 (2005).
Labhasetwar, "Nanoparticle drug delivery system for restenosis", Advanced Drug Delivery Reviews, 24:63-85 (1997).
Labhasetwar, et al., "Arterial uptake of biodegradable nanoparticles: effect of surface modifications", J Pharm Sci, 87:1229-1234(1998).
Lamprecht, et al., "Biodegradable nanoparticles for targeted drug delivery in treatment of inflammatory bowel disease", J Pharmacel Exp Ther, 299(2)775-81 (2001).
Langer, et al., "New advances in microsphere-based single-dose vaccines," Adv. Drug Deliv. Rev.,#s(28#1):97-119 (1997).
Langer and Folkman, "Polymers for the sustained release of proteins and other macromolecules", Nature, 263(5580):797-800(1976).
Lathia, et al., "Polymeric contrast agent with targeting potential", Ultrasonics, 42 (1-9):763-8 (2004).
Lavik, et al., "A simple synthetic route to the formation of a block copolymer of poly(lactic-co-glycolic acid) and polylysine for the fabrication of functionalized, degradable structures for biomedical applications", J Biomed Mater Res, 58(3):291-4 (2001).
Linblad, "Aluminum adjuvantsin retrospect and prospect," Vaccine, 22(27#2D (29#:3658-68 (2004).
Liu, et al., Abstracts of Papers of the American Chemical Society, 216.U875-U875 (1998).
Lopes De Menezes, et al., "In vitro and in vivo targeting of immunoliposomal doxorubicin to human B-cell lymphoma", Cancer Res, 58:3320-3330 (1998).
Luo, "Polyethylene gfycol)-Conjugated PAMAM Dendrimer for Biocompatible, High-Efficiency DNA Delivery", Macromolecules, 35:3456-3462 (2002).
Luo, et al., "Controlled DNA delivery system", Phar. Res., 16:1300-1308(1999).
Mader, et al., "Monitoring microviscosity and microacidity of the albumin microenvironment inside degrading microparticles from poly(lactide-co-glycolide) (PLG) or ABA-triblock polymers containing hydrophobic poly(lactide-co-glycolide) A blocks and hydrophilic poly(ethyleneoxide) B blocks", Pharm Res, 15(5):787-93 1994.
Mainardes, et al., "Colloidal carriers for ophthalmic drug delivery", CurrDrug Targets, 6:363-371 (2005).
Maloy, et al., "Induction of mucosal and systemic immune responses by immunization with ovalbumin entrapped in poly(lactide-co-glycolide) microparticles," Immunology, 81(4):661-7 (1994).
Marx, et al., "Protection against vaginal SIV transmission with microencapsulated vaccine," Science, 260(5112): 1323-7 (1992).
McPhail, "Liposomes encapsulating polymeric chitosan based vesicles—a vesicle in vesicle system for drug delivery", International Journal of Pharmaceutics, 200(1 ):73-86 (2000).
Mellman, et al., "Antigen processing and presentation by dendritic cells: cell biological mechanisms," Adv. Exp. Med. Biol., 560:63-7 (2005).
Mellman, et al., "Dendritic cells: specialized and regulated antigen processing machines," Cell, 106(3):255-8 (2001).
Moser, et al., "Virosomal adjuvanted antigen delivery systems," Expert Rev. Vaccines, 2(2):189-96 (2003).
Mu, et al, "Vitamin E TPGS used as emulsifier in the solvent evaporation /extraction technique for fabrication of polymeric nanospheresfor controlled release of paclitaxel (Taxol)", J Control Release, 80(1-3): 129-44 (2002).
Mu, et al., "A novel controlled release formulation for the anticancer drug paclitaxel (Taxol): PLGA nanoparticles containing vitamin E TPGS", J Control Release, 86(1):33-48 (2003).
Mueller, "Surface Modification of PLGA Microspheres", J Biomed Mater Res, 66A(1):55-61 (2003).
Mumper, et al., "Genetic immunization by jet injection of targeted pDNA-coated nanoparticles," Methods, 31(3):255-62 (2003).
Naylor, et al., "Starburst Dendrimers. 5. Molecular Shape Control", Journal of the American Chemical Society, 111:2339-2341 (1989).
Nellore, et al., "Evaluation of biodegradable microspheres as vaccine adjuvant for hepatitis B surface antigen," J. Parenter. Sci. Technol. 46(5):176-80 (1992).
Nunn, et al., "Complement inhibitor of C5 activation from the soft tick *Omithodoros moubata*", J Immunol, 174(4):2084-91 (2005).
O'Hagan, et al., "Long-term antibody responses in mice following subcutaneous immunization with ovalbumin entrapped in biodegradable microparticles," Vaccine, 11(9):965-969 (1993).
O'Hagan, et al., "Recent advances in the discovery and delivery of vaccine adjuvants," War. Rev. Drug Discov., 2(9):727-35 (2003).
Olivier, "Drug transport to brain with targeted nanoparticles", NeuroRx, 2:108-119 (2005).
Pan, et al., "Strategy for the treatment of myelogenous leukemia based on folate receptor p-targeted liposomal doxorubicin combined with receptor induction using all-frans retinoic acid", 6/oocf, 100:594-602 (2002).
Panyam, "Biodegradable nanoparticles for drug and gene delivery to cells and tissue", Adv Drug Deliv Rev, 55(3):329-47 (2003).
Panyam, et al., "Rapid endo-lysosomal escape of poly(DL-lactide-co-glycolide) nanoparticles: implications for drug and gene delivery," FASEB J., 16(10): 1217-26 (2002).
Park, et al., "Anti-HER2 immunoliposomes: enhanced efficacy attributable to targeted delivery" Clin Cancer Res, 8:1172-1181 (2002).
Park, et al., "Integration of surface modification and#s=s#fabrication techniques to prepare patterned poly(L-lactide) substrate allowing regionally selective cell adhesion", J Biomater Sci Polym Ed, 9(2):89-110 (1998).
Park, et al., "Surface modified poly(lactide-co-glycolide) nanospheres for targeted bone imaging with enhanced labeling and delivery of radio isotope", J Biomed Mater Res, 67A (3):751-60 (2003).
Pashine, et al., "Targeting the innate immune response with improved vaccine adjuvants," Nat. Med., 11(4 Suppl):S63-8 (2005).
Pastorino, et al., "Doxorubicin-loaded Fab' fragments of anti-disialoganglioside immunoliposomes selectively inhibit the growth and dissemination of human neuroblastoma in nude mice", Cancer Res, 63(1):86-92 (2003).
Pitaksuteepong, et al., "Uptake of antigen encapsulated in polyethylcyanoacrylate nanoparticles by D1-dendtitic cells," Pharmazie, 59(2):134-42 (2004).
Quirk, et al., "Cell-type-specific adhesion onto polymer surfaces from mixed cell populations", Biotech Bioeng, 81(5):625-628 (2003).
Schiffelers, et al., "Cancer siRNA therapy by tumor selective delivery with ligand-targeted sterically stabilized nanoparticle", Nucleic Acids Res, 32: e149 (2004).
Schneck, "Monitoring antigen-specific T cells using MHC-Ig dimmers", Immunol Invest,#s)3A#163-9 (2000).
Sesardic, et al., "European union regulatory developments for new vaccine adjuvants and delivery systems," Vaccine, 22(19):2452-6 (2004).
Shen, et al., "Enhanced and prolonged cross-presentation following endosomal escape of exogenous antigens encapsulated in biodegradable nanoparticles," Immunity, 117(1):78-88 (2006).
Shenderova, et al., "The acidic microclimate in poly(lactide-co-glycolide) microspheres stabilizes camptothecins", PharmRes, 16(2):241-8 (1999).
Singh, et al., "Advances in vaccine adjuvants for infectious diseases," Curr. HIV Res., 1(3):309-20 (2003).

(56) References Cited

OTHER PUBLICATIONS

Singh, et al., "Controlled release microparticles as a single dose diphtheria toxoid vaccine: immunogenicity in small animal models," Vaccine, 16(4):346-52 (1998).

Singh, et al., "Immunogenicity and protection in small-animal models with controlled-release tetanus toxoid microparticles as a single-dose vaccine," Infect. Immun., 65(5):1716-21 (1997).

Singh, et al., "Immunogenicity studies on diphtheria toxoid loaded biodegradable microspheres," Int. J. Pharmaceutics, 85(1-3):R5-R8 (1992).

Singh, et al., "Recent advances in vaccine adjuvants," Pharm. Res., 19(6):715#2D(s#(2002).

Song, et al., "Arterial uptake of biodegradable nanoparticles for intravascular local drug delivery: results with an acute dog model", J Control Release, 54:201-211 (1998).

Storni, et al., "Immunity in response to particulate antigen delivery systems," Adv. Drug Deliv. Rev., 57(3):333-55 (2005).

Summerton, "Endo-Porter: A Novel Reagent for Safe, Effective Delivery of Substances into Cells," Ann. N.Y. Acad. Sci., 1058:1-14(2005).

Sykulev, et al., "High-affinity reactions between antigen-specific T-cell receptors and peptides associated with allogeneic and syngeneic major histocompatibility complex class I proteins", Proc Natl Acad Sci U S A, 91:11487-91 (1994).

Tanaka, et al "Structure of FK506: a novel immunosuppressant isolated from a Streptomyces", J. Am. Chem. Soc, 109:5031-5033(1987).

Thomasin, et al., "Drug microencapsulation by PLA/PLGA coacervation in the light of thermodynamics. 1. Overview and theoretical considerations", J Pharm Sci, 87(3):259-68 (1998).

Tomalia, et al., "Starburst dendrimers: Molecular level control of size, shape, surface chemistry, topology and flexibility of atoms to macroscopic matter", Angewandte Chemie-International Edition in English,#s)3A#138-175 (1990).

Van Der Lubben, et al., "Chitosan for mucosal vaccination," Adv. Drug Deliv. Rev., 52(2):139-44 (2001).

Visscher, et al., "Biodegradation of and tissue reaction to 50:50 poly(DL-lactide-co-glycolide) microcapsules", J Biomed Mater Res, 19(3):349-65 (1985).

Wan, et al., "Characterization of surface property of poly(lactide-co-glycolide) after oxygen plasma treatment", Biomatehals, 25(19):4777-83 (2004).

Wang, et al., "Preparation and characterization of poly(lactic-co-glycolic acid) microspheres for targeted delivery of a novel anti-cancer agent, taxol", Chem Pharm Bull (Tokyo), 44(10): 1935-40 (1996).

Wartlick, et al., "Highly specific HER2-mediated cellular uptake of antibody-modified nanoparticles in tumour cells" J Drug Target, 12:461-471 (2004).

Wassef et al., "Liposomes as carriers for vaccines," Immunomethods, 4(3):217-22 (1994).

Wikingsson, et al., "Polyacryl starch microparticles as adjuvant in oral immunization, inducing mucosal and systemic immune responses in mice," Vaccine, 20(27#2D(29#:3355-63 (2002).

Yamaguchi and Anderson, "In vivo biocompatibility studies of medisorb 65/35 D, L-lactide/glycolide copolymer microspheres", J. Controlled Re/., 24(1-3):81-93(1993).

Yang, et al., "Plasma-treated, collagen-anchored polylactone: Its cell affinity evaluation under shear or shear-free conditions", J Biomed Mater Res, 67A(4): 1139-47 (2003).

Yoo, et al., "PAMAM dendrimers as delivery agents for antisense oligonucleotides", Pharm Res, 16:1799-804 (1999).

Zheng, et al., "Production of microspheres with surface amino groups from blends of Poly (Lactide-co-glycolide) and Poly(epsilon-CBZ-L-lysine) and use for encapsulation", Biotechnology Progress, 15(4):763-767 (1999).

Sehgal, et al., "Nanoparticle-medicated combinatorial targeting of multiple human dendritic cell (DC) subsets leads to enhanced T cell activation via IL-15-dependent DC crosstalk", J Immunol., 193:2297-305 (2014).

Demento, et al., Inflammasome-activating nanoparticles as modular systems for optimizing vaccine efficacy, Vaccine, 27(23):3013-21 (2009). doi: 10.1016/j.vaccine.2009.03.034. Epub Apr. 3, 2009.

Fischer, et al., "Conjugation to nickel-chelating nanolipoprotein particles increases the potency and efficacy of subunit vaccines to prevent West Nile encephalitis," Bioconjug Chem., 21(6):1018-22 (2010) doi: 10.1021/bc100083d.

International Search Report in PCT/US2015/059711, published Jun. 16, 2016.

Mallajosyula, et al., "Single-dose monomeric HA subunit vaccine generates full protection from influenza challenge," Hum Vaccin Immunother, 10(3):586-95 (2014). Epub Dec. 30, 2013.

\* cited by examiner

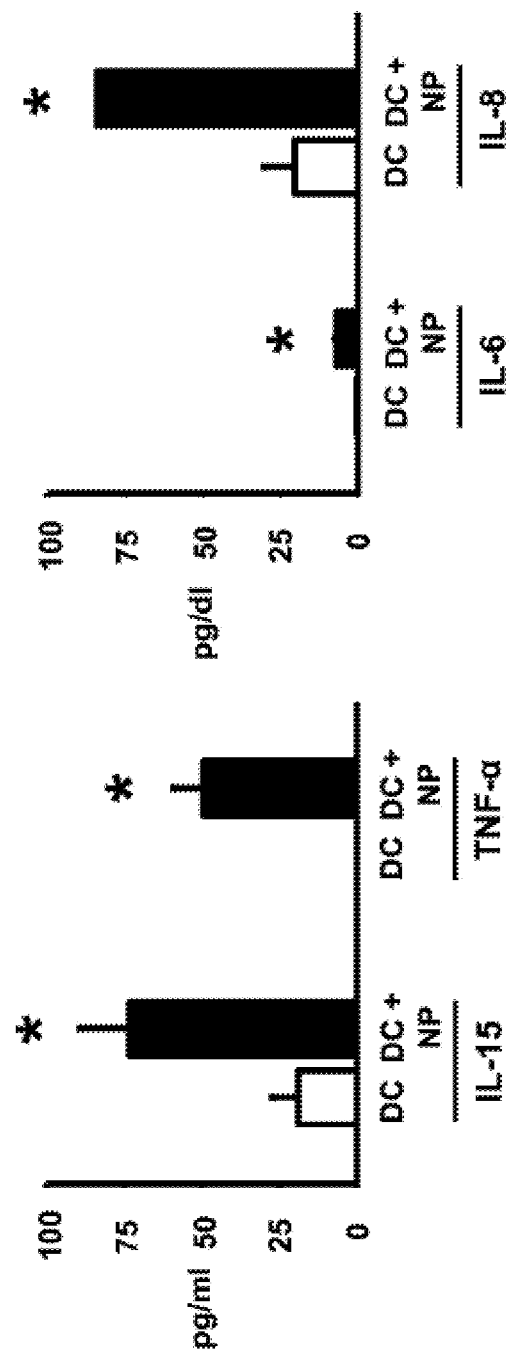

SEQUENCE LISTING

```
<160> NUMBER OF SEQ ID NOS: 40

<210> SEQ ID NO 1
<211> LENGTH: 14
<212> TYPE: PRT
<213> ORGANISM: Artificial Sequence
<220> FEATURE:
<223> OTHER INFORMATION: SOX2 Peptide

<400> SEQUENCE: 1

Leu Gly Ala Glu Trp Lys Leu Leu Ser Glu Thr Glu Lys Arg
1               5                   10

<210> SEQ ID NO 2
<211> LENGTH: 14
<212> TYPE: PRT
<213> ORGANISM: Artificial Sequence
<220> FEATURE:
<223> OTHER INFORMATION: SOX2 Peptide

<400> SEQUENCE: 2

Glu Trp Lys Leu Leu Ser Glu Thr Glu Lys Arg Pro Phe Ile
1               5                   10

<210> SEQ ID NO 3
<211> LENGTH: 15
<212> TYPE: PRT
<213> ORGANISM: Artificial Sequence
<220> FEATURE:
<223> OTHER INFORMATION: SOX2 Peptide

<400> SEQUENCE: 3

Leu Leu Ser Glu Thr Glu Lys Arg Pro Phe Ile Asp Glu Ala Lys
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: SOX2 Peptide

<400> SEQUENCE: 4

Thr Glu Lys Arg Pro Phe Ile Asp Glu Ala Lys Arg Leu Arg Ala
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: SOX2 Peptide

<400> SEQUENCE: 5

Pro Phe Ile Asp Glu Ala Lys Arg Leu Arg Ala Leu His Met Lys
1               5                   10                  15

<210> SEQ ID NO 6
```

```
<211> LENGTH: 13
<212> TYPE: PRT
<213> ORGANISM: Artificial Sequence
<220> FEATURE:
<223> OTHER INFORMATION: SOX2 Peptide

<400> SEQUENCE: 6

Glu Ala Lys Arg Leu Arg Ala Leu His Met Lys Glu His
1               5                   10

<210> SEQ ID NO 7
<211> LENGTH: 15
<212> TYPE: PRT
<213> ORGANISM: Artificial Sequence
<220> FEATURE:
<223> OTHER INFORMATION: SOX2 Peptide

<400> SEQUENCE: 7

Lys Arg Leu Arg Ala Leu His Met Lys Glu His Pro Asp Tyr Lys
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: SOX2 Peptide

<400> SEQUENCE: 8

Ala Leu His Met Lys Glu His Pro Asp Tyr Lys Tyr Arg Pro Arg
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: SOX2 Peptide

<400> SEQUENCE: 9

Lys Glu His Pro Asp Tyr Lys Tyr Arg Pro Arg Arg Lys Thr Lys
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: SOX2 Peptide

<400> SEQUENCE: 10

Asp Tyr Lys Tyr Arg Pro Arg Arg Lys Thr Lys Thr Leu Met Lys
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: SOX2 Peptide

<400> SEQUENCE: 11

Arg Pro Arg Arg Lys Thr Lys Thr Leu Met Lys Lys Asp Lys Tyr
1               5                   10                  15

<210> SEQ ID NO 12
<211> LENGTH: 15
```

```
<212> TYPE: PRT
<213> ORGANISM: Artificial Sequence
<220> FEATURE:
<223> OTHER INFORMATION: SOX2 Peptide

<400> SEQUENCE: 12

Lys Thr Lys Thr Leu Met Lys Lys Asp Lys Tyr Thr Leu Pro Gly
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: SOX2 Peptide

<400> SEQUENCE: 13

Leu Met Lys Lys Asp Lys Tyr Thr Leu Pro Gly Gly Leu Leu Ala
1               5                   10                  15

<210> SEQ ID NO 14
<211> LENGTH: 14
<212> TYPE: PRT
<213> ORGANISM: Artificial Sequence
<220> FEATURE:
<223> OTHER INFORMATION: SOX2 Peptide

<400> SEQUENCE: 14

Asp Lys Tyr Thr Leu Pro Gly Gly Leu Leu Ala Pro Gly Gly
1               5                   10

<210> SEQ ID NO 15
<211> LENGTH: 15
<212> TYPE: PRT
<213> ORGANISM: Artificial Sequence
<220> FEATURE:
<223> OTHER INFORMATION: SOX2 Peptide

<400> SEQUENCE: 15

Thr Leu Pro Gly Gly Leu Leu Ala Pro Gly Gly Asn Ser Met Ala
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: SOX2 Peptide

<400> SEQUENCE: 16

Gly Leu Leu Ala Pro Gly Gly Asn Ser Met Ala Ser Gly Val Gly
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: SOX2 Peptide

<400> SEQUENCE: 17

Pro Gly Gly Asn Ser Met Ala Ser Gly Val Gly Val Gly Ala Gly
1               5                   10                  15

<210> SEQ ID NO 18
<211> LENGTH: 15
<212> TYPE: PRT
```

```
<213> ORGANISM: Artificial Sequence
<220> FEATURE:
<223> OTHER INFORMATION: SOX2 Peptide

<400> SEQUENCE: 18

Ser Met Ala Ser Gly Val Gly Val Gly Ala Gly Leu Gly Ala Gly
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: SOX2 Peptide

<400> SEQUENCE: 19

Gly Val Gly Val Gly Ala Gly Leu Gly Ala Gly Val Asn Gln Arg
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: SOX2 Peptide

<400> SEQUENCE: 20

Gly Ala Gly Leu Gly Ala Gly Val Asn Gln Arg Met Asp Ser Tyr
1               5                   10                  15

<210> SEQ ID NO 21
<211> LENGTH: 14
<212> TYPE: PRT
<213> ORGANISM: Artificial Sequence
<220> FEATURE:
<223> OTHER INFORMATION: SOX2 Peptide

<400> SEQUENCE: 21

Gly Ala Gly Val Asn Gln Arg Met Asp Ser Tyr Ala His Met
1               5                   10

<210> SEQ ID NO 22
<211> LENGTH: 15
<212> TYPE: PRT
<213> ORGANISM: Artificial Sequence
<220> FEATURE:
<223> OTHER INFORMATION: SOX2 Peptide

<400> SEQUENCE: 22

Val Asn Gln Arg Met Asp Ser Tyr Ala His Met Asn Gly Trp Ser
1               5                   10                  15

<210> SEQ ID NO 23
<211> LENGTH: 9
<212> TYPE: PRT
<213> ORGANISM: Artificial Sequence
<220> FEATURE:
<223> OTHER INFORMATION: CEF Peptide

<400> SEQUENCE: 23

Val Ser Asp Gly Gly Pro Asn Leu Tyr
1               5

<210> SEQ ID NO 24
<211> LENGTH: 9
<212> TYPE: PRT
<213> ORGANISM: Artificial Sequence
```

```
<220> FEATURE:
<223> OTHER INFORMATION: CEF Peptide

<400> SEQUENCE: 24

Gly Leu Cys Thr Leu Val Ala Met Leu
1               5

<210> SEQ ID NO 25
<211> LENGTH: 9
<212> TYPE: PRT
<213> ORGANISM: Artificial Sequence
<220> FEATURE:
<223> OTHER INFORMATION: CEF Peptide

<400> SEQUENCE: 25

Gly Ile Leu Gly Phe Val Phe Thr Leu
1               5

<210> SEQ ID NO 26
<211> LENGTH: 9
<212> TYPE: PRT
<213> ORGANISM: Artificial Sequence
<220> FEATURE:
<223> OTHER INFORMATION: CEF Peptide

<400> SEQUENCE: 26

Ile Leu Arg Gly Ser Val Ala His Lys
1               5

<210> SEQ ID NO 27
<211> LENGTH: 9
<212> TYPE: PRT
<213> ORGANISM: Artificial Sequence
<220> FEATURE:
<223> OTHER INFORMATION: CEF Peptide

<400> SEQUENCE: 27

Arg Val Arg Ala Tyr Thr Tyr Ser Lys
1               5

<210> SEQ ID NO 28
<211> LENGTH: 9
<212> TYPE: PRT
<213> ORGANISM: Artificial Sequence
<220> FEATURE:
<223> OTHER INFORMATION: CEF Peptide

<400> SEQUENCE: 28

Arg Leu Arg Ala Glu Ala Gln Val Lys
1               5

<210> SEQ ID NO 29
<211> LENGTH: 9
<212> TYPE: PRT
<213> ORGANISM: Artificial Sequence
<220> FEATURE:
<223> OTHER INFORMATION: CEF Peptide

<400> SEQUENCE: 29

Ile Val Thr Asp Phe Ser Val Ile Lys
1               5

<210> SEQ ID NO 30
<211> LENGTH: 9
<212> TYPE: PRT
<213> ORGANISM: Artificial Sequence
<220> FEATURE:
```

```
<223> OTHER INFORMATION: CEF Peptide

<400> SEQUENCE: 30

Ala Thr Ile Gly Thr Ala Met Tyr Lys
1               5

<210> SEQ ID NO 31
<211> LENGTH: 10
<212> TYPE: PRT
<213> ORGANISM: Artificial Sequence
<220> FEATURE:
<223> OTHER INFORMATION: CEF Peptide

<400> SEQUENCE: 31

Asp Tyr Cys Asn Val Leu Asn Lys Glu Phe
1               5                   10

<210> SEQ ID NO 32
<211> LENGTH: 9
<212> TYPE: PRT
<213> ORGANISM: Artificial Sequence
<220> FEATURE:
<223> OTHER INFORMATION: CEF Peptide

<400> SEQUENCE: 32

Lys Thr Gly Gly Pro Ile Tyr Lys Arg
1               5

<210> SEQ ID NO 33
<211> LENGTH: 9
<212> TYPE: PRT
<213> ORGANISM: Artificial Sequence
<220> FEATURE:
<223> OTHER INFORMATION: CEF Peptide

<400> SEQUENCE: 33

Arg Pro Pro Ile Phe Ile Arg Arg Leu
1               5

<210> SEQ ID NO 34
<211> LENGTH: 9
<212> TYPE: PRT
<213> ORGANISM: Artificial Sequence
<220> FEATURE:
<223> OTHER INFORMATION: CEF Peptide

<400> SEQUENCE: 34

Gln Ala Lys Trp Arg Leu Gln Thr Leu
1               5

<210> SEQ ID NO 35
<211> LENGTH: 9
<212> TYPE: PRT
<213> ORGANISM: Artificial Sequence
<220> FEATURE:
<223> OTHER INFORMATION: CEF Peptide

<400> SEQUENCE: 35

Phe Leu Arg Gly Arg Ala Tyr Gly Leu
1               5

<210> SEQ ID NO 36
<211> LENGTH: 8
<212> TYPE: PRT
<213> ORGANISM: Artificial Sequence
<220> FEATURE:
<223> OTHER INFORMATION: CEF Peptide
```

```
<400> SEQUENCE: 36

Arg Ala Lys Phe Lys Gln Leu Leu
1               5

<210> SEQ ID NO 37
<211> LENGTH: 9
<212> TYPE: PRT
<213> ORGANISM: Artificial Sequence
<220> FEATURE:
<223> OTHER INFORMATION: CEF Peptide

<400> SEQUENCE: 37

Arg Arg Ile Tyr Asp Leu Ile Glu Leu
1               5

<210> SEQ ID NO 38
<211> LENGTH: 9
<212> TYPE: PRT
<213> ORGANISM: Artificial Sequence
<220> FEATURE:
<223> OTHER INFORMATION: CEF Peptide

<400> SEQUENCE: 38

Ser Arg Tyr Trp Ala Ile Arg Thr Arg
1               5

<210> SEQ ID NO 39
<211> LENGTH: 9
<212> TYPE: PRT
<213> ORGANISM: Artificial Sequence
<220> FEATURE:
<223> OTHER INFORMATION: CEF Peptide

<400> SEQUENCE: 39

Tyr Pro Leu His Glu Gln His Gly Met
1               5

<210> SEQ ID NO 40
<211> LENGTH: 10
<212> TYPE: PRT
<213> ORGANISM: Artificial Sequence
<220> FEATURE:
<223> OTHER INFORMATION: CEF Peptide

<400> SEQUENCE: 40

Glu Phe Phe Trp Asp Ala Asn Asp Ile Tyr
1               5                   10
```

MODULAR NANODEVICES FOR SMART ADAPTABLE VACCINES

CROSS-REFERENCE TO RELATED APPLICATIONS

This application is a continuation in part of U.S. Ser. No. 12/527,143, filed Aug. 13, 2009, under 35 U.S.C. § 371 of PCT/US2008/054086 filed on Feb. 15, 2008, which claims priority to and benefit of U.S. Provisional Patent Application No. 60/890,133 filed on Feb. 15, 2007 and U.S. Provisional Patent Application No. 61/000,016 filed on Oct. 23, 2007, and where permissible is incorporated by reference in its entirety.

STATEMENT REGARDING FEDERALLY SPONSORED RESEARCH

This invention was made with government support under 0609326 awarded by the National Science Foundation. The government has certain rights in the invention.

REFERENCE TO SEQUENCE LISTING

The Sequence Listing submitted on Aug. 8, 2014 as a text file named "YU_4549 CIP_ST25.txt," created on Dec. 1, 2014, and having a size of 8,952 bytes is hereby incorporated by reference pursuant to 37 C.F.R. § 1.52(e)(5).

FIELD OF THE INVENTION

The present disclosure generally relates to the field of modular nano-scale vaccine compositions and methods of making and using these compositions.

BACKGROUND OF THE INVENTION

Preventative vaccines have eliminated smallpox and nearly eliminated polio, two of the worst global infectious diseases. By contrast vaccines for many other infectious diseases, such as malaria and HIV, which involve intracellular pathogens, are poorly developed or simply unavailable (Singh and O'Hagan, *Pharm. Res.*, 19(6):715-28 (2002); O'Hagan and Valiante, *Nat. Rev. Drug Discov.*, 2(9):727-35 (2003)). The lack of such vaccines results in two million unnecessary deaths each year in many parts of the world (WHO, State of the Art New Vaccines (2003)).

Several key variables are needed in the design of effective vaccines (Pashine, et al., *Nat. Med.*, 11(4 Suppl):563-8 (2005), Bramwell and Perrie, *Drug Discovery Today*, 10(22):1527-34 (2005)). The first variable is the form of the antigen itself, which can be whole inactivated or attenuated organisms, purified proteins and peptides, or DNA encoded antigens. Human pathogens are continually emerging and changing (e.g. SARS, avian flu) meaning that new potential immunogens are constantly appearing. Thus, there is a clear need to design vaccine systems that can rapidly and efficiently test the efficacy of vaccines involving new antigens (Bramwell, et al., *Adv. Drug Deliv. Rev.* 57(9):1247-65 (2005)). Large scale and safe production of stable vaccine products typically involves the purification of natural or recombinant forms of antigenic subunits. Once purified, however, individual antigens often become less immunogenic compared to whole pathogens or crude extracts, necessitating a means to amplify the immune response against the purified subunit antigen. Thus, a second necessary component of a vaccine involves providing an adjuvant or other means for potentiating or stimulating both the innate and adaptive arms of the immune system to the antigen subunit (Pashine, et al., *Nat. Med.*, 11(4 Suppl):563-8 (2005), Bramwell and Perrie, *Drug Discovery Today*, 10(22):1527-34 (2005)).

Immune potentiators may include bacterial products, toxins or other molecules that augment specific immunity. Potentiators have various benefits, but also attendant risks such as triggering deleterious inflammatory responses. To affect optimal stimulation to a given antigen, a formulation is needed that delivers the correct amount of antigen in a repetitive or sustained fashion, to the appropriate immune cells and to the appropriate compartments within those cells. Thus, a designed delivery vehicle (adjuvant) should target the vaccine antigen and facilitate delivery of both antigen and immune potentiating molecules selectively to target cells of the immune system. This is highly reminiscent of the strategy taken by viruses that inactivate specific components of the immune system during infection. Traditional methods for increasing the effectiveness of vaccines have focused on co-administration of adjuvants or use of a delivery system.

While the adjuvant role is critical, there are obvious risks, costs and limitations associated with this traditional approach. For example, currently available adjuvants, represented predominately by colloidal alum (aluminum sulfate or aluminum hydroxide) or montanide polymers, have a limited capacity to adsorb many antigens and have greatly limited immunostimulatory properties (Gupta and Siber, *Vaccine*, 13(14):1263-76 (1995); Lindblad, *Vaccine*, 22(27-28):3658-68 (2004)). There are also risks associated with using live attenuated vaccines and allergic side effects associated with aluminum salts (Lindblad, *Vaccine*, 22(27-28):3658-68 (2004); Gupta, et al., *Vaccine*, 11(3):293-306 (1993)). Additionally, because of the historical emphasis on eliciting humoral immune responses, most adjuvants are optimized for effective induction of high antibody serum titers, but are ineffective at eliciting a strong cellular, T cell-mediated immune response or strong mucosal immune response. T cell responses are essential for inducing lasting viral immunity (or immune responses to cancer); mucosal immunity is essential for protective responses to cellular and viral pathogens that are transmitted through mucosal surfaces (e.g. human immunodeficiency virus, HIV; herpes simplex virus, HSV; enteric pathogens). These factors, coupled with the difficulties of manufacture, storage, and transport have together greatly limited the utility of current approaches in the clinic and in the field (O'Hagan and Valiante, *Nat. Rev. Drug Discov.*, 2(9):727-35 (2003); Sigh and Srivastava, Curr. HIV Res., 1(3):309-20 (2003), Singh and O'Hagan, *Nat. Biotechnol.*, 17(11):1075-81 (1999)).

Thus, in addition to economic factors, as outlined above, there are a number of significant scientific challenges that have limited the development of vaccines for deadly diseases. First, few if any approaches are available that efficiently prime cell-mediated immunity by direct intracellular delivery of an antigen. Second, 'tunable' adjuvants, that is, adjuvants that can be engineered to optimize the magnitude and direction of an immune response (Jiang, et al., *Adv. Drug Deliv. Rev.*, 57(3):391-410 (2005); Sesardic and Dobbelaer, *Vaccine*, 22(19):2452-6 (2004)) have not been developed. Third, alternatives are not available for the general requirement for parenteral (i.e. subcutaneous or intramuscular injection) administration of vaccines, a situation that has made it difficult to deploy vaccines in underdeveloped countries where medical support systems, resources, and cold-storage are limited. Finally, there is no general approach to designing oral vaccines targeted to both systemic and mucosal immunity. This would be highly advantageous since oral vaccines are significantly less expensive to administer and transport. Thus, there is a critical need for safe and stable vaccine systems that would address all these factors (Friede and Aguado, *Adv. Drug Deliv. Rev.*, 57(3): 325-31 (2005); Storni, et al., *Adv. Drug Deliv. Rev.*, 57(3): 333-55 (2005); Gupta, et al., *Adv. Drug Deliv. Rev.*, 32(3): 225-246 (1998); Aguado and Lambert, *Immunobiology*, 184 (2-3):113-25 (1992)).

It is therefore an object of the invention to provide stable vaccine formulations which can be orally administered.

It is another object of the invention to provide modular nanoparticulate vaccine compositions which provide for flexible addition and subtraction of elements.

It is still another object of the invention to provide means for modulating an immune response, either to increase or decrease the response, or bias the response to a humoral or cellular immune response.

It is a further object of the invention to provide methods for making and using such modular nanoparticulate vaccine compositions.

SUMMARY OF THE INVENTION

Modular nanoparticle vaccine compositions and methods of making and using them have been developed. The modular design of these nanoparticle vaccine compositions, which involves flexible addition and subtraction of antigen, adjuvant and/or immune potentiators, molecular recognition factors, and transport mediation elements, as well as intracellular uptake mediators, allows for exquisite control over many of the variables that are important for optimizing an effective vaccine delivery system. A key feature of these nanodevices is their ability to be selectively targeted to those cells of the immune system that are most closely associated with producing the desired immunological response for a given vaccine. This is accomplished by encapsulating any vaccine antigen within the nanoparticles, together with the activators of the desired immune activity. The nanoparticle surface is then modified by the direct or indirect coupling of targeting molecules, such as antibodies, that guide the entire nanodevice to specific cell types (such as dendritic cells) associated with stimulating or suppressing immune responses. The targeted particles are constructed to bind to the intended cell type, to be internalized by endocytosis, and then to dissociate, thereby releasing the encapsulated antigen and immune activators (adjuvants). The modular nature of the nanodevice enables rapid production and the ability to modify the nanoparticle surface with any of a variety of targeting molecules, enabling targeting to different cell types, such as various dendritic cell subsets, epithelial cells, or macrophages. The adjuvant composition can also be easily altered to enable the systematic assessment of optimal targeting and composition for any desired application. The nanodevices can be easily characterized biochemically using conventional ELISA and flow cytometry assays, and by in vitro or in vivo assays for antigen presentation and immune stimulation.

Modular nanoparticle vaccine compositions include an antigen incorporated or encapsulated in a polymeric nanoparticle. Antigens may be viral, bacterial, parasitic, allergen, toxoid, tumor-specific or tumor-associated antigens, which can be one or more proteins, carbohydrates, lipids, nucleic acids, or combinations thereof. The nanoparticle further includes adaptor elements which modularly couple functional elements to the particle. In the preferred embodiment, the adaptor elements are fatty acids, hydrophobic or amphipathic peptides, or hydrophobic polymers. Adaptor elements can be conjugated to affinity tags, which allow for modular assembly and disassembly of functional elements which are conjugated to complementary affinity tags to the nanoparticle. Functional elements impart useful functions to the nanoparticle compositions. Functional elements may include, for example, dendritic cell targeting molecules, epithelial cell targeting molecules, pH-sensitive or non-pH-sensitive molecules which protect the vaccine composition from hydrolysis and degradation in low pH environments, and endosome-disrupting agents. Nanoparticle vaccine compositions may further include adjuvants, contrast agents and other markers and pharmaceutically acceptable excipients.

The ability to target exogenous antigens to internalizing surface molecules on antigen-presenting cells facilitates the uptake of antigens and their presentation to lymphocytes and thus overcomes a major rate-limiting step in vaccination. The ability to target vaccine compositions to epithelial cells in the digestive tract greatly facilitates the ability of a vaccine to induce mucosal and systemic immunity when administered orally. Molecules which protect the vaccine composition from hydrolysis and degradation in low pH environments also enhance the efficacy of vaccines administered orally. Endosome-disrupting agents function to cause limited disruption of endosome-lysosome membranes during antigen uptake by antigen-presenting cells. This allows the antigen to enter the cytoplasm and be presented on MHC class I molecules on the surface of antigen-presenting cells in a process known as cross-presentation. Cross-presentation allows for the activation of cytotoxic CD8 positive T cells which greatly enhances the effectiveness of vaccination. The modular nanoparticulate vaccine compositions offer several advantages over other vaccines: 1) targeting of different cells, thereby enabling optimal selection of different tissue and priming for antigen presentation; 2) delivery of a wide variety of antigens of clinical importance; and 3) rapid assembly of different combinations of protective, recognition and antigen modules to affect a broad-spectrum potent vaccine response.

BRIEF DESCRIPTION OF THE DRAWINGS

FIGS. 11A-11D are bar graphs showing mean cytokine expression levels (IL-15, IFN-λ and TNF-α in pg/ml, and IL-6 and IL-8 in pg/dl, ±SEM) per 30,000 APCs for BDCA3+ or DC-SIGN+DC subsets obtained from three different healthy donors.

DETAILED DESCRIPTION OF THE INVENTION

Figure 1:
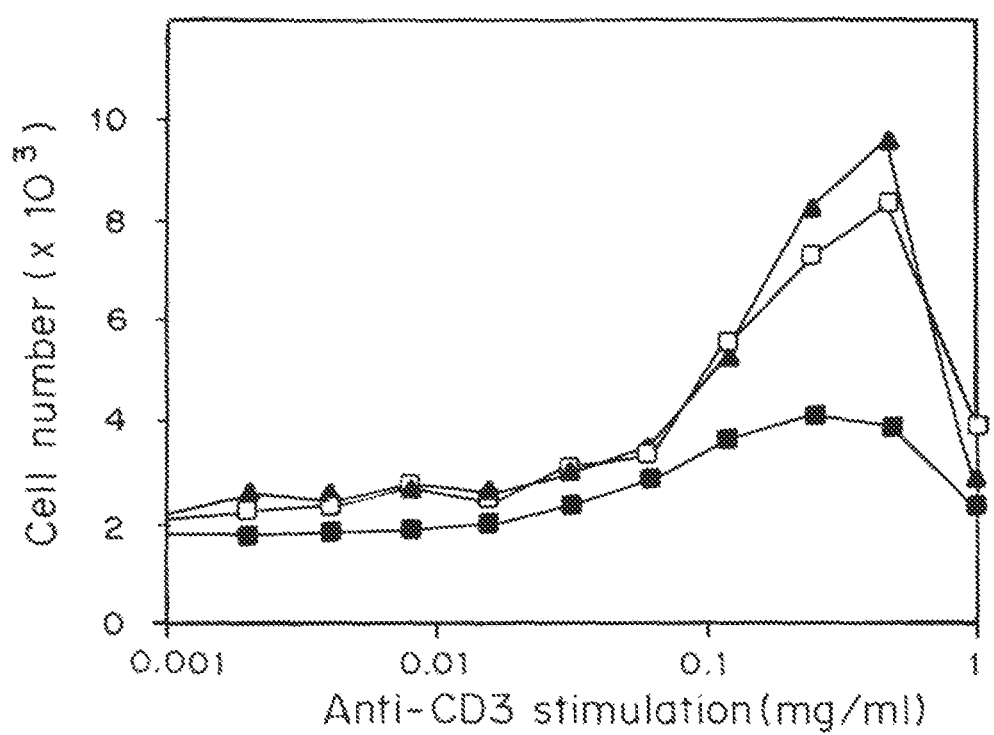
FIG. 1 is a graph demonstrating inhibition of CD3-stimulated T-cell proliferation (number of cells) when T-cells are exposed to doxorubicin-loaded particles modified with an antibody (-■-) that recognizes T-cells at the indicated concentration (mg/ml). Controls are doxorubicin-loaded nanoparticles without antibody (-□-) and blank nanoparticles (-▲-).

A solution to the vaccine problem requires a systematic approach that addresses each of the design challenges discussed above. Viruses and pathogens that elicit or subvert immune responses are, in essence, small particles endowed with the ability to interact with or avoid cells of the immune system in a variety of ways. The vaccines described herein are based on an approach in which nanoscale modules are assembled into units that are optimized for stimulating immune responses to a specific pathogen. The principles of nanoassembly is used to design safe vaccine vectors that are highly optimized to protect against disease and provide new treatment options for disorders such as asthma, allergy, and cancer.

I. Definitions

"Affinity tags" are defined herein as molecular species which form highly specific, non-covalent, physiochemical interactions with defined binding partners. Affinity tags which form highly specific, non-covalent, physiochemical interactions with one another are defined herein as "complementary".

"Adaptor elements" are defined herein as molecular entities which associate with polymeric nanoparticles and provide substrates that facilitate the modular assembly and disassembly of functional elements onto the nanoparticle. Adaptor elements can be conjugated to affinity tags. Affinity tags allow for flexible assembly and disassembly of functional elements which are conjugated to affinity tags that form highly specific, noncovalent, physiochemical interactions with affinity tags conjugated to adaptor elements. Adaptor elements can also be covalently coupled to functional elements in the absence of affinity tags.

"Functional elements" are defined herein as molecular entities which associate with nanoparticles and impart a particular function to the nanoparticle. Functional elements can associate with nanoparticles through adaptor elements, or through direct association with the nanoparticle surface. Functional elements can be conjugated to affinity tags which form highly specific, noncovalent, physiochemical interactions with complementary affinity tags conjugated to adaptor elements. Thus, functional elements can be coupled to adaptor elements noncovalently through affinity tags. Alternatively, functional elements can be covalently coupled to adaptor elements in the absence of affinity tags. Functional elements can also be covalently or noncovalently associated with the surface of nanoparticles without the use of adaptor elements.

An "antigen" is defined herein as a molecule which contains one or more epitopes that will stimulate a host's immune system to make a cellular antigen-specific immune response, and/or a humoral antibody response. Antigens can be peptides, proteins, polysaccharides, saccharides, lipids, nucleic acids, and combinations thereof. The antigen can be derived from a virus, bacterium, parasite, plant, protozoan, fungus, tissue or transformed cell such as a cancer or leukemic cell and can be a whole cell or immunogenic component thereof, e.g., cell wall components. An antigen may be an oligonucleotide or polynucleotide which expresses an antigen. Antigens can be natural or synthetic antigens, for example, haptens, polyepitopes, flanking epitopes, and other recombinant or synthetically derived antigens (Bergmann, et al., *Eur. J. Immunol.*, 23:2777-2781 (1993); Bergmann, et al., *J. Immunol.*, 157:3242-3249 (1996); Suhrbier, *Immunol. and Cell Biol.*, 75:402-408 (1997).

A "tumor-specific antigen" is defined herein as an antigen that is unique to tumor cells and does not occur in or on other cells in the body.

A "tumor-associated antigen" is defined herein as an antigen that is not unique to a tumor cell and is also expressed in or on a normal cell under conditions that fail to induce an immune response to the antigen.

An "adjuvant" is defined herein as a substance increasing the immune response to other antigens when administered with other antigens. Adjuvants are also referred to herein as "immune potentiators" and "immune modulators".

"Antigen-presenting cells" are defined herein as highly specialized cells that can process antigens and display their peptide fragments on the cell surface together with molecules required for lymphocyte activation. The major antigen-presenting cells for T cells are dendritic cells, macrophages and B cells. The major antigen-presenting cells for B cells are follicular dendritic cells.

"Cross-presentation" is defined herein as the ability of antigen-presenting cells to take up, process and present extracellular antigens with MHC class I molecules to CD8 T cells (cytotoxic T cells). This process induces cellular immunity against most tumors and against viruses that do not infect antigen-presenting cells. Cross-presentation is also required for induction of cytotoxic immunity by vaccination with protein antigens, for example in tumor vaccination.

An "endosome-disrupting agent" is defined herein as any agent which causes disruption of endosomal membranes during endocytosis. Endosome-disrupting agents facilitate the transit of extracellular antigens into the cytoplasm of antigen-presenting cells, where they can be imported into the endoplasmic reticulum and processed for cross-presentation on MHC class I molecules at the cell surface.

"Dendritic cell targeting molecules" are defined herein as molecules that target and facilitate endocytosis of nanoparticles by dendritic cells. Dendritic cell targeting molecules may be directly coupled to nanoparticles, or may be coupled to nanoparticles through adaptor elements. In a preferred embodiment the dendritic cell targeting molecules are functionally coupled to adaptor elements.

"Epithelial cell targeting molecules" are defined herein as molecules that target the nanoparticles to epithelium and mediate transcytosis to underlying antigen-presenting cells. Epithelial cell targeting molecules may be directly coupled to nanoparticles, or may be coupled to nanoparticles through adaptor elements. In a preferred embodiment the epithelial cell targeting molecules are functionally coupled to adaptor elements.

As used herein, the phrase that a molecule "specifically binds" to a target refers to a binding reaction which is determinative of the presence of the molecule in the presence of a heterogeneous population of other biologics. Thus, under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity. Specific binding between two entities means an affinity of at least $10^6$, $10^7$, $10^8$, $10^9$, or $10^{10}$ $M^{-1}$. Affinities greater than $10^8$ $M^{-1}$ are preferred.

As used herein, the terms "antibody" or "immunoglobulin" are used to include intact antibodies and binding fragments thereof. Typically, fragments compete with the intact antibody from which they were derived for specific binding to an antigen fragment including separate heavy chains, light chains Fab, Fab' F(ab')2, Fabc, and Fv. Fragments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992).

As used herein, the terms "epitope" or "antigenic determinant" refer to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids, in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed. (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., J. Inf. Dis. 170, 1110-19 (1994)), by antigen-dependent killing (cytotoxic T lymphocyte assay, Tigges et al., J. Immunol. 156, 3901-3910) or by cytokine secretion.

As used herein, the terms "immunologic", "immunological" or "immune" response is the development of a humoral (antibody mediated) and/or a cellular (mediated by antigen-specific T cells or their secretion products) response directed against an antigen. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific $CD4^+$ T helper cells and/or $CD8^+$ cytotoxic T cells. The response may also involve activation of monocytes, macrophages, NK cells, basophils, dendritic cells, astrocytes, microglia cells, eosinophils or other components of innate immunity. The presence of a cell-mediated immunological response can be determined by proliferation assays ($CD4^+$ T cells) or CTL (cytotoxic T lymphocyte) assays. The relative contributions of humoral and cellular responses to the protective or therapeutic effect of an immunogen can be distinguished by separately isolating antibodies and T-cells from an immunized syngeneic animal and measuring protective or therapeutic effect in a second subject.

As used herein, a "costimulatory polypeptide" or a "costimulatory molecule" is a polypeptide that, upon interaction with a cell-surface molecule on T cells, enhances T cell responses, enhances proliferation of T cells, enhances production and/or secretion of cytokines by T cells, stimulates differentiation and effector functions of T cells or promotes survival of T cells relative to T cells not contacted with a costimulatory peptide.

The terms "individual", "host", "subject", and "patient" are used interchangeably herein, and refer to a mammal, including, but not limited to, murines, simians, humans, mammalian farm animals, mammalian sport animals, and mammalian pets.

II. Modular Nanoparticulate Vaccine Compositions

Modular nanodevice vaccine systems are constructed from nanoparticles. The modular design of these nanoparticle vaccine compositions, which involves flexible addition and subtraction of antigen, adjuvant, immune potentiators, molecular recognition, and/or transport mediation elements, as well as intracellular uptake mediators, allows for exquisite control over many of the variables that are important for optimizing an effective vaccine delivery system.

A. Polymeric Nanoparticles

As used herein, nanoparticles generally refers to particles in the range of between 500 nm to less than 0.5 nm, preferably having a diameter that is between 50 and 500 nm.

The polymer that forms the core of the modular vaccine nanoparticle may be any biodegradable or non-biodegradable synthetic or natural polymer. In a preferred embodiment, the polymer is a biodegradable polymer. These systems have several features that make them ideal materials for the fabrication of a vaccine nanodevice: 1) control over the size range of fabrication, down to 100 nm or less, an important feature for passing through biological barriers; 2) reproducible biodegradability without the addition of enzymes or cofactors; 3) capability for sustained release of an encapsulated, protected antigen over a period in the range of days to months by varying factors such as the monomer ratios or polymer size, for example, poly(lactic acid) (PLA) to poly(glycolic acid) (PGA) copolymer ratios, potentially abrogating the booster requirement (Gupta, et al., *Adv. Drug Deliv. Rev.*, 32(3):225-246 (1998); Kohn, et al., *J. Immunol. Methods*, 95(1):31-8 (1986); Langer, et al., *Adv. Drug Deliv. Rev.*, 28(1):97-119 (1997); Jiang, et al., *Adv. Drug Deliv. Rev.*, 57(3):391-410)), well-understood fabrication methodologies that offer flexibility over the range of parameters that can be used for fabrication, including choices of the polymer material, solvent, stabilizer, and scale of production; and 5) control over surface properties facilitating the introduction of modular functionalities into the surface.

Examples of preferred biodegradable polymers include synthetic polymers that degrade by hydrolysis such as poly(hydroxy acids), such as polymers and copolymers of lactic acid and glycolic acid, polyanhydrides, poly(ortho) esters, polyesters, polyurethanes, poly(butic acid), poly(valeric acid), poly(caprolactone), poly(hydroxyalkanoates), and poly(lactide-co-caprolactone).

Preferred natural polymers include alginate and other polysaccharides, collagen, albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

In some embodiments, non-biodegradable polymers can be used, especially hydrophobic polymers. Examples of preferred non-biodegradable polymers include ethylene vinyl acetate, poly(meth) acrylic acid, copolymers of maleic anhydride with other unsaturated polymerizable monomers, poly(butadiene maleic anhydride), polyamides, copolymers and mixtures thereof, and dextran, cellulose and derivatives thereof.

Other suitable biodegradable and non-biodegradable polymers include, but are not limited to, polyanhydrides, polyamides, polycarbonates, polyalkylenes, polyalkylene oxides such as polyethylene glycol, polyalkylene terephthalates such as poly(ethylene terephthalate), polyvinyl alcohols, polyvinyl ethers, polyvinyl esters, polyethylene, polypropylene, poly(vinyl acetate), poly vinyl chloride, polystyrene, polyvinyl halides, polyvinylpyrrolidone, polymers of acrylic and methacrylic esters, polysiloxanes, polyurethanes and copolymers thereof, modified celluloses, alkyl cellulose, hydroxyalkyl celluloses, cellulose ethers, cellulose esters, nitro celluloses, cellulose acetate, cellulose propionate, cellulose acetate butyrate, cellulose acetate phthalate, carboxyethyl cellulose, cellulose triacetate, cellulose sulfate sodium salt, and polyacrylates such as poly(methyl methacrylate), poly(ethylmethacrylate), poly(butylmethacrylate), poly(isobutylmethacrylate), poly(hexylmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate).

The foregoing materials may be used alone, as physical mixtures (blends), or as co-polymers. In a preferred embodiment, the nanoparticle is formed of polymers fabricated from polylactides (PLA) and copolymers of lactide and glycolide (PLGA). These have established commercial use in humans and have a long safety record (Jiang, et al., *Adv. Drug Deliv. Rev.*, 57(3):391-410); Aguado and Lambert, *Immunobiology*, 184(2-3):113-25 (1992); Bramwell, et al., *Adv. Drug Deliv. Rev.*, 57(9):1247-65 (2005)).

The polymer may be a bioadhesive polymer that is hydrophilic or hydrophobic. Hydrophilic polymers include CARBOPOL™ (a high molecular weight, crosslinked, acrylic acid-based polymers manufactured by NOVEON™), polycarbophil, cellulose esters, and dextran.

Rate controlling polymers may be included in the polymer matrix or in the coating on the formulation. Examples of rate controlling polymers that may be used are hydroxypropylmethylcellulose (HPMC) with viscosities of either 5, 50, 100 or 4000 cps or blends of the different viscosities, ethylcellulose, methylmethacrylates, such as EUDRAGIT® RS100, EUDRAGIT® RL100, EUDRAGIT® NE 30D (supplied by Rohm America). Gastrosoluble polymers, such as EUDRAGIT® E100 or enteric polymers such as EUDRAGIT® L100-55D, L100 and 5100 may be blended with rate controlling polymers to achieve pH dependent release kinetics. Other hydrophilic polymers such as alginate, polyethylene oxide, carboxymethylcellulose, and hydroxyethylcellulose may be used as rate controlling polymers.

These polymers can be obtained from sources such as Sigma Chemical Co., St. Louis, Mo.; Polysciences, Warrenton, Pa.; Aldrich, Milwaukee, Wis.; Fluka, Ronkonkoma, N.Y.; and BioRad, Richmond, Calif., or can be synthesized from monomers obtained from these or other suppliers using standard techniques.

B. Antigens

Antigens can be peptides, proteins, polysaccharides, saccharides, lipids, glycolipids, nucleic acids, or combinations thereof. The antigen can be derived from ant source, including, but not limited to, a virus, bacterium, parasite, plant, protozoan, fungus, tissue or transformed cell such as a cancer or leukemic cell and can be a whole cell or immunogenic component thereof, e.g., cell wall components or molecular components thereof.

Suitable antigens are known in the art and are available from commercial government and scientific sources. In one embodiment, the antigens are whole inactivated or attenuated organisms. These organisms may be infectious organisms, such as viruses, parasites and bacteria. These organisms may also be tumor cells. The antigens may be purified or partially purified polypeptides derived from tumors or viral or bacterial sources. Criteria for identifying and selecting effective antigenic peptides (e.g., minimal peptide sequences capable of eliciting an immune response) can be found in the art. For example, Apostolopoulos, et al. (*Curr. Opin. Mol. Ther.*, 2:29-36 (2000)), discusses the strategy for identifying minimal antigenic peptide sequences based on an understanding of the three-dimensional structure of an antigen-presenting molecule and its interaction with both an antigenic peptide and T-cell receptor. Shastri, (*Curr. Opin. Immunol.*, 8:271-7 (1996)), disclose how to distinguish rare peptides that serve to activate T cells from the thousands peptides normally bound to MHC molecules. The antigens can be recombinant polypeptides produced by expressing DNA encoding the polypeptide antigen in a heterologous expression system. The antigens can be DNA encoding all or part of an antigenic protein. The DNA may be in the form of vector DNA such as plasmid DNA.

Antigens may be provided as single antigens or may be provided in combination. Antigens may also be provided as complex mixtures of polypeptides or nucleic acids.

i. Viral Antigens

A viral antigen can be isolated from any virus including, but not limited to, a virus from any of the following viral families: Arenaviridae, Arterivirus, Astroviridae, Baculoviridae, Badnavirus, Barnaviridae, Birnaviridae, Bromoviridae, Bunyaviridae, Caliciviridae, Capillovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (e.g., Zaire, Reston, Ivory Coast, or Sudan strain)), Flaviviridae, (e.g., Hepatitis C virus, Dengue virus 1, Dengue virus 2, Dengue virus 3, Dengue virus 4, and West Nile virus), Hepadnaviridae, Herpesviridae (e.g., Human herpesvirus 1, 3, 4 (Epstein-Barr virus), 5, and 6, and Cytomegalovirus), Hypoviridae, Iridoviridae, Leviviridae, Lipothrixviridae, Microviridae, Orthomyxoviridae (e.g., Influenzavirus A and B and C), Papovaviridae, Paramyxoviridae (e.g., measles, mumps, and human respiratory syncytial virus), Parvoviridae, Picornaviridae (e.g., poliovirus, rhinovirus, hepatovirus, and aphthovirus), Poxviridae (e.g., vaccinia and smallpox virus), Reoviridae (e.g., rotavirus), Retroviridae (e.g., lentivirus, such as human immunodeficiency virus (HIV) 1 and HIV 2), Rhabdoviridae (for example, rabies virus, measles virus, respiratory syncytial virus, etc.), Togaviridae (for example, rubella virus, dengue virus, etc.), and Totiviridae. Suitable viral antigens also include all or part of Dengue protein M, Dengue protein E, Dengue D1NS1, Dengue D1NS2, and Dengue D1NS3.

Viral antigens may be derived from a particular strain such as a papilloma virus, a herpes virus, i.e. herpes simplex 1 and 2; a hepatitis virus, for example, hepatitis A virus (HAV), hepatitis B virus (HBV), hepatitis C virus (HCV), the delta hepatitis D virus (HDV), hepatitis E virus (HEV) and hepatitis G virus (HGV), the tick-borne encephalitis viruses; parainfluenza, varicella-zoster, cytomeglavirus, Epstein-Barr, rotavirus, rhinovirus, adenovirus, coxsackieviruses, equine encephalitis, Japanese encephalitis, yellow fever, Rift Valley fever, and lymphocytic choriomeningitis.

ii. Bacterial Antigens

Bacterial antigens can originate from any bacteria including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus, Hemophilus* influenza type B (HIB), *Hyphomicrobium, Legionella, Leptspirosis, Listeria, Meningococcus* A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus*, and *Treponema, Vibrio*, and *Yersinia*.

iii. Parasite Antigens

Parasite antigens can be obtained from parasites such as, but not limited to, an antigen derived from *Cryptococcus neoformans, Histoplasma capsulatum, Candida albicans, Candida tropicalis, Nocardia asteroides, Rickettsia* ricketsii, *Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis* and *Schistosoma mansoni*. These include Sporozoan antigens, Plasmodian antigens, such as all or part of a Circumsporozoite protein, a Sporozoite surface protein, a liver stage antigen, an apical membrane associated protein, or a Merozoite surface protein.

iv. Allergens and Environmental Antigens

The antigen can be an allergen or environmental antigen, such as, but not limited to, an antigen derived from naturally occurring allergens such as pollen allergens (tree-, herb, weed-, and grass pollen allergens), insect allergens (inhalant, saliva and venom allergens), animal hair and dandruff allergens, and food allergens. Important pollen allergens from trees, grasses and herbs originate from the taxonomic orders of Fagales, Oleales, Pinales and platanaceae including, i.e., birch (*Betula*), alder (*Alnus*), hazel (*Corylus*), hornbeam (*Carpinus*) and olive (*Olea*), cedar (*Cryptomeriaand Juniperus*), Plane tree (*Platanus*), the order of Poales including, i.e., grasses of the genera *Lolium, Phleum, Poa, Cynodon, Dactylis, Holcus, Phalaris, Secale*, and Sorghum, the orders of Asterales and Urticales including, i.e., herbs of the genera *Ambrosia, Artemisia*, and *Parietaria*. Other allergen antigens that may be used include allergens from house dust mites of the genus *Dermatophagoides* and *Euroglyphus*, storage mite, e.g., *Lepidoglyphys, Glycyphagus* and *Tyrophagus*, those from cockroaches, midges and fleas e.g., *Blatella, Periplaneta, Chironomus* and Ctenocepphalides, those from mammals such as cat, dog and horse, birds, venom allergens including such originating from stinging or biting insects such as those from the taxonomic order of Hymenoptera including bees (superfamily Apidae), wasps (superfamily Vespidea), and ants (superfamily Formicoidae). Still other allergen antigens that may be used include inhalation allergens from fungi such as from the genera *Alternaria* and *Cladosporium*.

v. Tumor Antigens

The antigen can be a tumor antigen, including a tumor-associated or tumor-specific antigen, such as, but not limited to SOX2, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-All, hsp70-2, KIAAO205, Mart2, Mum-1, 2, and 3, neo-PAP, myosin class I, OS-9, pml-RARa fusion protein, PTPRK, K-ras, N-ras, Triosephosphate isomeras, Bage-1, Gage 3,4,5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\70K, NY-CO-1, RCAS1, SDCCAG16, TA-90 (Mac-2 binding protein\cyclophilin C-associated protein), TAAL6, TAG72, TLP, and TPS.

C. Adaptor Elements

Adaptor elements associate with the nanoparticle and provide substrates that facilitate the modular assembly and disassembly of functional elements to the nanoparticle. Adaptor elements may associate with nanoparticles through a variety of interactions including, but not limited to, hydrophobic interactions, electrostatic interactions and covalent coupling.

In a preferred embodiment, the adaptor elements associate with the polymeric nanoparticles noncovalently through hydrophobic interactions. Examples of adaptor elements which may associate with nanoparticles via hydrophobic interactions include, but are not limited to, fatty acids, hydrophobic or amphipathic peptides or proteins, and polymers. These classes of adaptor elements may also be used in any combination or ratio. In a preferred embodiment, the association of adaptor elements with nanoparticles facilitates a prolonged presentation of functional elements which can last for several weeks.

Adaptor elements can also be attached to polymeric nanoparticles through covalent interactions through various functional groups. Functionality refers to conjugation of a molecule to the surface of the particle via a functional chemical group (carboxylic acids, aldehydes, amines, sulfhydryls and hydroxyls) present on the surface of the particle and present on the molecule to be attached.

Functionality may be introduced into the particles in two ways. The first is during the preparation of the nanoparticles, for example during the emulsion preparation of nanoparticles by incorporation of stabilizers with functional chemical groups. Suitable stabilizers include hydrophobic or amphipathic molecules that associate with the outer surface of the nanoparticles.

A second is post-particle preparation, by direct crosslinking particles and ligands with homo- or heterobifunctional crosslinkers. This second procedure may use a suitable chemistry and a class of crosslinkers (CDI, EDAC, glutaraldehydes, etc. as discussed in more detail below) or any other crosslinker that couples ligands to the particle surface via chemical modification of the particle surface after preparation. This second class also includes a process whereby amphiphilic molecules such as fatty acids, lipids or functional stabilizers may be passively adsorbed and adhered to the particle surface, thereby introducing functional end groups for tethering to ligands.

One useful protocol involves the "activation" of hydroxyl groups on polymer chains with the agent, carbonyldiimidazole (CDI) in aprotic solvents such as DMSO, acetone, or THF. CDI forms an imidazolyl carbamate complex with the hydroxyl group which may be displaced by binding the free amino group of a molecule such as a protein. The reaction is an N-nucleophilic substitution and results in a stable N-alkylcarbamate linkage of the molecule to the polymer. The "coupling" of the molecule to the "activated" polymer matrix is maximal in the pH range of 9-10 and normally requires at least 24 hrs. The resulting molecule-polymer complex is stable and resists hydrolysis for extended periods of time.

Another coupling method involves the use of 1-ethyl-3-(3-dimethylaminopropyl) carbodiimide (EDAC) or "water-soluble CDI" in conjunction with N-hydroxylsulfosuccinimide (sulfo NHS) to couple the exposed carboxylic groups of polymers to the free amino groups of molecules in a totally aqueous environment at the physiological pH of 7.0. Briefly, EDAC and sulfo-NHS form an activated ester with the carboxylic acid groups of the polymer which react with the amine end of a molecule to form a peptide bond. The resulting peptide bond is resistant to hydrolysis. The use of sulfo-NHS in the reaction increases the efficiency of the EDAC coupling by a factor of ten-fold and provides for exceptionally gentle conditions that ensure the viability of the molecule-polymer complex.

By using either of these protocols it is possible to "activate" almost all polymers containing either hydroxyl or carboxyl groups in a suitable solvent system that will not dissolve the polymer matrix.

A useful coupling procedure for attaching molecules with free hydroxyl and carboxyl groups to polymers involves the use of the cross-linking agent, divinylsulfone. This method would be useful for attaching sugars or other hydroxylic compounds with bioadhesive properties to hydroxylic matrices. Briefly, the activation involves the reaction of divinylsulfone to the hydroxyl groups of the polymer, forming the vinylsulfonyl ethyl ether of the polymer. The vinyl groups will couple to alcohols, phenols and even amines. Activation and coupling take place at pH 11. The linkage is stable in the pH range from 1-8 and is suitable for transit through the intestine.

Any suitable coupling method known to those skilled in the art for the coupling of molecules and polymers with double bonds, including the use of UV crosslinking, may be used for attachment of molecules to the polymer.

In one embodiment adaptor elements can be conjugated to affinity tags. Affinity tags are any molecular species which form highly specific, noncovalent, physiochemical interactions with defined binding partners. Affinity tags which form highly specific, noncovalent, physiochemical interactions with one another are defined herein as "complementary". Suitable affinity tag pairs are well known in the art and include epitope/antibody, biotin/avidin, biotin/streptavidin, biotin/neutravidin, glutathione-S-transferase/glutathione, maltose binding protein/amylase and maltose binding protein/maltose. Examples of suitable epitopes which may be used for epitope/antibody binding pairs include, but are not limited to, HA, FLAG, c-Myc, glutatione-S-transferase, $His_6$, GFP, DIG, biotin and avidin. Antibodies (both monoclonal and polyclonal and antigen-binding fragments thereof) which bind to these epitopes are well known in the art.

Affinity tags that are conjugated to adaptor elements allow for highly flexible, modular assembly and disassembly of functional elements which are conjugated to affinity tags which form highly specific, noncovalent, physiochemical interactions with complementary affinity tags which are conjugated to adaptor elements. Adaptor elements may be conjugated with a single species of affinity tag or with any combination of affinity tag species in any ratio. The ability to vary the number of species of affinity tags and their ratios conjugated to adaptor elements allows for exquisite control over the number of functional elements which may be attached to the nanoparticles and their ratios.

In another embodiment adaptor elements are coupled directly to functional elements in the absence of affinity tags, such as through direct covalent interactions. Adaptor elements can be covalently coupled to at least one species of functional element. Adaptor elements can be covalently coupled to a single species of functional element or with any combination of species of functional elements in any ratio.

In a preferred embodiment adaptor elements are conjugated to at least one affinity tag that provides for assembly and disassembly of modular functional elements which are conjugated to complementary affinity tags. In a more preferred embodiment, adaptor elements are fatty acids that are conjugated with at least one affinity tag. In a particularly preferred embodiment, the adaptor elements are fatty acids conjugated with avidin or streptavidin. Such avidin/streptavidin-conjugated fatty acids allow for the attachment of a wide variety of biotin-conjugated functional elements.

The adaptor elements are provided on, or in the surface of, nanoparticles at a high density. This high density of adaptor elements allows for coupling of the nanoparticle to a variety of species of functional elements while still allowing for the functional elements to be present in high enough numbers to be efficacious.

i. Fatty Acids

The adaptor elements may include fatty acids. Fatty acids may be of any acyl chain length and may be saturated or unsaturated. In a particularly preferred embodiment the fatty acid is palmitic acid. Other suitable fatty acids include, but are not limited to, saturated fatty acids such as butyric, caproic, caprylic, capric, lauric, myristic, stearic, arachidic and behenic acid. Still other suitable fatty acids include, but are not limited to, unsaturated fatty acids such as oleic, linoleic, alpha-linolenic, arachidonic, eicosapentaenoic, docosahexaenoic and erucic acid.

ii. Hydrophobic or Amphipathic Peptides

The adaptor elements may include hydrophobic or amphipathic peptides. Preferred peptides should be sufficiently hydrophobic to preferentially associate with the polymeric nanoparticle over the aqueous environment. Amphipathic polypeptides useful as adaptor elements may be mostly hydrophobic on one end and mostly hydrophilic on the other end. Such amphipathic peptides may associate with polymeric nanoparticles through the hydrophobic end of the peptide and be conjugated on the hydrophilic end to a functional group.

iii. Hydrophobic Polymers

Adaptor elements may include hydrophobic polymers. Examples of hydrophobic polymers include, but are not limited to, polyanhydrides, poly(ortho)esters, and polyesters such as polycaprolactone.

D. Functional Elements

Functional elements which associate with the nanoparticles provide a number of different functions to the composition. These functions include protection of the nanoparticle vaccine from hostile environments during transit in the gastrointestinal tract, transport through epithelial barriers, targeting antigen presenting cells (APCs) with high avidity, and transport of mediators that facilitate uptake and presentation of antigen by antigen-presenting cells through disruption of intracellular antigen-sequestering compartments. Functional elements may include dendritic cell recognition elements, epithelial cell recognition elements, pH-sensitive molecules which protect the composition from hydrolysis and degradation in low-pH environments, non-pH-sensitive molecules which protect the composition from hydrolysis and degradation in low-pH environments, and/or endosome-disrupting agents.

Nanoparticles may be associated with a single species of functional element or may be associated with any combination of disclosed functional elements in any ratio. In one embodiment, functional elements are directly associated with nanoparticles in the absence of adaptor elements. Functional elements may be directly associated with nanoparticles through covalent or noncovalent interactions, including, but not limited to, hydrophobic interactions and electrostatic interactions. Covalent attachment of functional elements can be achieved by introducing functionality to the polymeric nanoparticles using methods described above with respect to adaptor elements.

In another embodiment, functional elements are associated with nanoparticles through adaptor elements which directly associate with the nanoparticles. Functional elements may be directly, covalently coupled to adaptor elements or may couple to adaptor elements through complementary affinity tags conjugated to the adaptor and functional elements. Multiple different species of functional elements may be associated with nanoparticles in any desired ratio, for instance, by conjugating each species of functional element to a separate species of affinity tag. These functional elements may then associate with nanoparticles coated with adaptor elements conjugated to an appropriate ratio of complementary affinity tags. Multiple species of functional elements may also be associated with nanoparticles by covalently coupling each species of functional element at a desired ratio to adaptor elements.

In a preferred embodiment, functional elements are conjugated to biotin. Biotin conjugation allows the functional elements to interact with adaptor elements conjugated with avidin, neutravidin or streptavidin.

i. Targeting Molecules for Professional Antigen Presenting Cells

Of the main types of antigen-presenting cells (B cell, macrophages and DCs), the DC is the most potent and is responsible for initiating all antigen-specific immune responses. One biological feature of DCs is their ability to sense conditions under which antigen is encountered, initiating a process of "DC maturation". Using receptors for various microbial and inflammatory products, DCs respond to antigen exposure in different ways depending on the nature of the pathogen (virus, bacteria, protozoan) encountered. This information is transmitted to T cells by altered patterns of cytokine release at the time of antigen presentation in lymph nodes, altering the type of T cell response elicited. Thus, targeting DCs provides the opportunity not only to quantitatively enhance the delivery of antigen and antigen responses in general, but to qualitatively control the nature of the immune response depending on the desired vaccination outcome.

Dendritic cells express a number of cell surface receptors that can mediate the endocytosis of bound antigen. Targeting exogenous antigens to internalizing surface molecules on systemically-distributed antigen presenting cells facilitates uptake of antigens and thus overcomes a major rate-limiting step in immunization and thus in vaccination.

Dendritic cell targeting molecules include monoclonal or polyclonal antibodies or fragments thereof that recognize and bind to epitopes displayed on the surface of dendritic cells. Dendritic cell targeting molecules also include ligands which bind to a cell surface receptor on dendritic cells. One such receptor, the lectin DEC-205, has been used in vitro and in mice to boost both humoral (antibody-based) and cellular (CD8 T cell) responses by 2-4 orders of magnitude (Hawiger, et al., J. Exp. Med., 194(6):769-79 (2001); Bonifaz, et al., *J. Exp. Med.,* 196(12):1627-38 (2002); Bonifaz, et al., *J. Exp. Med.,* 199(6):815-24 (2004)). In these experiments, antigens were fused to an anti-DEC205 heavy chain and a recombinant antibody molecule was used for immunization.

A variety of other endocytic receptors, including a mannose-specific lectin (mannose receptor) and IgG Fc receptors, have also been targeted in this way with similar enhancement of antigen presentation efficiency. Other suitable molecules which may be targeted include, but are not limited to, DC-SIGN, BDCA3 (CD141), 33D1, SIGLEC-H, DCIR, CD11c, heat shock protein receptors and scavenger receptors.

Other receptors which may be targeted include the toll-like receptors (TLRs). TLRs recognize and bind to pathogen-associated molecular patterns (PAMPs). PAMPs target the TLR on the surface of the dendritic cell and signals internally, thereby potentially increasing DC antigen uptake, maturation and T-cell stimulatory capacity. PAMPs conjugated to the particle surface or co-encapsulated include unmethylated CpG DNA (bacterial), double-stranded RNA (viral), lipopolysacharride (bacterial), peptidoglycan (bacterial), lipoarabinomannin (bacterial), zymosan (yeast), mycoplasmal lipoproteins such as MALP-2 (bacterial), flagellin (bacterial) poly(inosinic-cytidylic) acid (bacterial), lipoteichoic acid (bacterial) or imidazoquinolines (synthetic).

ii. Targeting Molecules for Epithelial Cells

The potential efficacy of nanoparticle vaccine systems is determined in part by their route of administration into the body. While injection (intradermal, intramuscular, intravenous) is an acceptable solution in many cases, having a vaccine product that is orally available will greatly extend its ease of use and applicability on a global scale. For orally administered vaccines, epithelial cells constitute the principal barrier that separates an organism's interior from the outside world. Epithelial cells such as those that line the gastrointestinal tract form continuous monolayers that simultaneously confront the extracellular fluid compartment and the extracorporeal space. Uptake by these gut epithelial cells can be enhanced, and the nanoparticles carried by "transcytosis" to the lymphatics where they have access to dendritic cells.

Through the process of "antigen sampling", underlying mucosal-associated lymphoid tissue sample the environment for the presence of pathogens. This sampling is carried out by an apical to basolateral transcytotic event and is mediated by M cells located in lymphoid follicle-associated epithelium (FAE) throughout the GI tract. In addition, absorptive enterocytes may transport microorganisms or other nanoparticulates to intraepithelial lymphocytes. DCs may perform this function directly, with a population of DCs being intercalated between epithelial cells and extending processes into the gut lumen to sample the microorganisms present.

Adherence to cells is an essential first step in crossing the epithelial barrier by any of these mechanisms. Therefore, in one embodiment, modular nanoparticle vaccines further include epithelial cell recognition elements. Epithelial cell targeting molecules include monoclonal or polyclonal antibodies or bioactive fragments thereof that recognize and bind to epitopes displayed on the surface of epithelial cells. Epithelial cell targeting molecules also include ligands which bind to a cell surface receptor on epithelial cells. Ligands include, but are not limited to, molecules such as polypeptides, nucleotides and polysaccharides.

A variety of receptors on epithelial cells may be targeted by epithelial cell targeting molecules. Examples of suitable receptors to be targeted include, but are not limited to, IgE Fc receptors, EpCAM, selected carbohydrate specificities, dipeptidyl peptidase, and E-cadherin.

iii. Coatings to Inhibit Degradation of Nanoparticle Vaccine Compositions in Extreme pH Environments Vaccine particles administered orally will encounter a corrosive environment in the gastrointestinal (GI) tract with areas of low and high pH, as well as resident degradative enzymes and solubilizing agents. Biodegradable particulates have gained attention as oral vaccines because of their ability to protect antigens on route to immune sites across the intestinal epithelium (O'Hagan and Valiante, *Nat. Rev. Drug Discov.,* 2(9):727-35 (2003); van der Lubben, et al., *Adv. Drug Deliv. Rev.,* 52(2):139-44 (2001); Wikingsson and Sjoholm, *Vaccine,* 20(27-28):3355-63 (2002); Moser, et al., *Expert Rev. Vaccines,* 2(2):189-96 (2003)). However, while the antigen is protected from environmental elements in transit, little protection is offered to elements coupled to the surface of the particle during the transit to immune effector sites. This protection may be necessary to insure proper particle function and targeting.

For this reason, 'shielding' is a desired feature to protect the nanoparticulate and its immune recognition elements in transit to the GI epithelium. This shielding may be environmentally-sensitive, i.e. pH responsive, or simply a protective layer. In a preferred embodiment, modular nanoparticle vaccines further include pH-sensitive molecules which protect the composition from hydrolysis and degradation in low pH environments. Such pH-sensitive protecting molecules are preferred because subsequent to the particles transit through a low pH environment, upon reaching its destination in the higher pH intestinal site, particles should expose epithelial targeting molecules to allow for specific interactions with target epithelial cells, followed by transcytosis through the epithelium and subsequent interactions with subepithelial dendritic cells.

Preferred non-pH-sensitive molecules which protect the composition from hydrolysis and degradation in low pH environments are poly(ethylene) glycol, gelatin and albumins.

Preferred pH-sensitive molecules which protect the composition from hydrolysis and degradation in low pH environments are elastin and poly(methacrylic) acid (PMAA). Both of these molecules are in extended conformations at pH 7.4 and shrink rapidly (within seconds) upon exposure to lower pH environments (below pH 5 for elastin and below pH 5-6 for poly(methacylic) acid). Other pH-sensitive molecules which may be used include poly(acrylic acid), poly (methyl methacrylic acid) and poly(N-alkyl acrylamides), or other enteric coatings discussed above.

pH-sensitive or pH-insensitive protective molecules may be directly coupled to nanoparticles, or may be coupled to nanoparticles through adaptor elements, such as those described above. In a preferred embodiment the epithelial cell targeting molecules are functionally coupled to adaptor elements.

E. Disruptors of Endosomal Compartments

Many receptors which may be used for targeting modular nanoparticle vaccines to dendritic cells, such as DEC-205, have the property of delivering antigens to late endosomal elements that serve as efficient sites for the formation of immunogenic peptides and their loading onto MHC class II molecules (which are needed for CD4 T cell and antibody responses) (Mellman, *Adv. Exp. Med. Biol.*, 560:63-7; Mellman and Steinman, *Cell*, 106(3):255-8 (2001)). Effective vaccination, however, often requires the production of CD8 cytotoxic T cell responses which occurs only when antigen is present in the cytoplasm. DCs are adept at this function by the process of "cross-presentation", whereby exogenous antigens escape endocytic vesicles and enter the cytoplasm where they are cleaved into peptides by the proteasome, imported into the endoplasmic reticulum, and loaded onto newly synthesized MHC class I molecules (which are required for stimulation of CD8 T cells).

It is possible to greatly enhance the efficiency of cross presentation by artificially causing the limited disruption of endosome-lysosome membranes during antigen uptake. In one embodiment, the modular nanoparticulate vaccine compositions include an agent which causes the disruption of endosomal membranes. Endosomal membrane disrupting agents include, but are not limited to, small molecule drugs, peptides, polypeptides, including elastin, and synthetic agents that disrupt intracellular pH or vesicular membranes.

Osmotic delivery is an endocytosis-mediated system for delivering large polar molecules into the cytosol of cells. The mechanism behind this process is also referred to as the "proton-sponge effect". The process renders the endosome fragile, releasing the contents of the endosome into the cytosol. Osmotic delivery and endosomal disruption work as follows: uptake of high-osmolarity cargo (typically charged substances) into newly forming endosomes renders their membranes fragile, which upon return to normal osmolarity after uptake, causes a net inflow of water into loaded endosomes resulting in build-up of pressure. This leads to an osmotic pressure within the endosomes and release of the cargo into the cytosol of the cell.

In a preferred embodiment, the endosome-disrupting agent is a low pH-activated, amphipathic, pore-forming peptide. In a particularly preferred embodiment, the low pH-activated, amphipathic, pore-forming peptide is the commercially-available Endoporter (Endoporter; Gene-Tools, Philomath, Oreg.) (Summerton, *Ann. N.Y. Acad. Sci.*, 1058:1-14 (2005)).

Agents other than Endoporter can mediate endosome disruption. Poly (lactic-co-glycolic acid) (PLGA) on its own can mediate this effect. This process can be increased by inclusion of other agents in PLGA. Other agents include charged macromolecules such as poly(amido amine) (PAMAM) dendrimers, or small molecule drugs such as carbonyl cyanide 4-(trifluoromethoxy)phenylhydrazone (FCCP), and oligonucleotides such as CpG. The endosome-disrupting agent may be encapsulated into the polymeric core of the nanoparticle. Additionally, or alternatively, the endosome-disrupting agent may be attached to the surface of the nanoparticle by association with attached adaptor elements.

G. Adjuvants

The modular nanoparticulate vaccines can include adjuvants. These can be incorporated into, administered with, or administered separately from, the vaccine nanoparticles. Adjuvants may be provided encapsulated or otherwise entrapped in the polymeric core of the nanoparticle vaccine, or may be associated with the surface of the nanoparticle either through direct association with the polymeric core, or through association with adaptor elements. Adjuvant may be in the form of separate nanoparticles or in a suspension or solution administered with the vaccine nanoparticles.

In one embodiment the adjuvant is the synthetic glycolipid alpha-galactosylceramide (αGalCer). Dendritic cells presenting antigens in the context of CD1d can lead to rapid innate and prolonged production of cytokines such as interferon and IL-4 by natural killer T cells (NKT cells). CD1d is a major histocompatibility complex class I-like molecule that presents glycolipid antigens to a subset of NKT cells. Advantageously, αGalCer is not toxic to humans and has been shown to act as an adjuvant, priming both antigen-specific CD4+ and CD8+ T cell responses. For example, it has been shown that αGalCer in conjunction with a malaria vaccine can lead to cytotoxic responses against infected cells, which is an ideal scenario for vaccines against infectious diseases. In addition to αGalCer, other glycolipids that function as adjuvants to activate NKT cell-mediated immune responses can be used.

In another embodiment the adjuvant can be, but is not limited to, one or more of the following: oil emulsions (e.g., Freund's adjuvant); saponin formulations; virosomes and viral-like particles; bacterial and microbial derivatives including, but not limited to, carbohydrates such as lipopolysachharide (LPS); immunostimulatory oligonucleotides; ADP-ribosylating toxins and detoxified derivatives; alum; BCG; mineral-containing compositions (e.g., mineral salts, such as aluminium salts and calcium salts, hydroxides, phosphates, sulfates, etc.); bioadhesives and/or mucoadhesives; microparticles; liposomes; polyoxyethylene ether and polyoxyethylene ester formulations; polyphosphazene; muramyl peptides; imidazoquinolone compounds; and surface active substances (e.g. lysolecithin, pluronic polyols, polyanions, peptides, oil emulsions, keyhole limpet hemocyanin, and dinitrophenol).

Adjuvants may also include immunomodulators such as cytokines, interleukins (e.g., IL-1, IL-2, IL-4, IL-5, IL-6, IL-7, IL-12, etc.), interferons (e.g., interferon-.gamma.), macrophage colony stimulating factor, and tumor necrosis factor; and co-stimulatory molecules, such as those of the B7 family. Such proteinaceous adjuvants may be provided as the full-length polypeptide or an active fragment thereof, or in the form of DNA, such as plasmid DNA.

H. Contrast Agents and Other Markers

Optionally, modular nanoparticulate vaccine may further include agents useful for determining the location of administered particles. Agents useful for this purpose include fluorescent tags, radionuclides and contrast agents.

Suitable imaging agents include, but are not limited to, fluorescent molecules such as those described by Molecular Probes (Handbook of fluorescent probes and research products), such as Rhodamine, fluorescein, Texas red, Acridine Orange, Alexa Fluor (various), Allophycocyanin, 7-aminoactinomycin D, BOBO-1, BODIPY (various), Calcien, Calcium Crimson, Calcium green, Calcium Orange, 6-carboxyrhodamine 6G, Cascade blue, Cascade yellow, DAPI, DiA, DiD, Dil, DiO, DiR, ELF 97, Eosin, ER Tracker Blue-White, EthD-1, Ethidium bromide, Fluo-3, Fluo4, FM1-43, FM4-64, Fura-2, Fura Red, Hoechst 33258, Hoechst 33342, 7-hydroxy-4-methylcoumarin, Indo-1, JC-1, JC-9, JOE dye, Lissamine rhodamine B, Lucifer Yellow CH, LysoSensor Blue DND-167, LysoSensor Green, LysoSensor Yellow/Blu, Lysotracker Green FM, Magnesium Green, Marina Blue, Mitotracker Green FM, Mitotracker Orange CMTMRos, MitoTracker Red CMXRos, Monobromobimane, NBD amines, NeruoTrace 500/525 green, Nile red, Oregon Green, Pacific Blue. POP-1, Propidium iodide, Rhodamine 110, Rhodamine Red, R-Phycoerythrin, Resorfin, RH414, Rhod-2, Rhodamine Green, Rhodamine 123, ROX dye, Sodium Green, SYTO blue (various), SYTO green (Various), SYTO orange (various), SYTOX blue, SYTOX green, SYTOX orange, Tetramethylrhodamine B, TOT-1, TOT-3, X-rhod-1, YOYO-1, YOYO-3.

Additionally radionuclides can be used as imaging agents. Suitable radionuclides include, but are not limited to radioactive species of Fe(III), Fe(II), Cu(II), Mg(II), Ca(II), and Zn(I1) Indium, Gallium and Technetium. Other suitable contrast agents include metal ions generally used for chelation in paramagnetic T1-type MIR contrast agents, and include di- and tri-valent cations such as copper, chromium, iron, gadolinium, manganese, erbium, europium, dysprosium and holmium. Metal ions that can be chelated and used for radionuclide imaging, include, but are not limited to metals such as gallium, germanium, cobalt, calcium, indium, iridium, rubidium, yttrium, ruthenium, yttrium, technetium, rhenium, platinum, thallium and samarium. Additionally metal ions known to be useful in neutron-capture radiation therapy include boron and other metals with large nuclear cross-sections. Also suitable are metal ions useful in ultrasound contrast, and X-ray contrast compositions.

Examples of other suitable contrast agents include gases or gas emitting compounds, which are radioopaque.

I. Pharmaceutically Acceptable Excipients

The compositions may be administered in combination with a physiologically or pharmaceutically acceptable carrier, excipient, or stabilizer. The term "pharmaceutically acceptable" means a non-toxic material that does not interfere with the effectiveness of the biological activity of the active ingredients. The term "pharmaceutically-acceptable carrier" means one or more compatible solid or liquid fillers, dilutants or encapsulating substances which are suitable for administration to a human or other vertebrate animal. The term "carrier" refers to an organic or inorganic ingredient, natural or synthetic, with which the active ingredient is combined to facilitate the application.

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen.

Optional pharmaceutically acceptable excipients include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (POLYPLASDONE® XL from GAF Chemical Corp).

Stabilizers are used to inhibit or retard decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-b-alanine, sodium N-lauryl-b-iminodipropionate, myristoamphoacetate, lauryl betaine and lauryl sulfobetaine.

If desired, the particles may also contain minor amount of nontoxic auxiliary substances such as wetting or emulsifying agents, dyes, pH buffering agents, or preservatives.

The particles may be complexed with other agents. The pharmaceutical compositions may take the form of, for example, tablets or capsules prepared by conventional means with pharmaceutically acceptable excipients such as binding agents (e.g., acacia, methylcellulose, sodium carboxymethylcellulose, polyvinylpyrrolidone (Povidone), hydroxypropyl methylcellulose, sucrose, starch, and ethylcellulose); fillers (e.g., corn starch, gelatin, lactose, acacia, sucrose, microcrystalline cellulose, kaolin, mannitol, dicalcium phosphate, calcium carbonate, sodium chloride, or alginic acid); lubricants (e.g. magnesium stearates, stearic acid, silicone fluid, talc, waxes, oils, and colloidal silica); and disintegrators (e.g. micro-crystalline cellulose, corn starch, sodium starch glycolate and alginic acid. If water-soluble, such formulated complex then may be formulated in an appropriate buffer, for example, phosphate buffered saline or other physiologically compatible solutions. Alternatively, if the resulting complex has poor solubility in aqueous solvents, then it may be formulated with a non-ionic surfactant such as TWEEN™, or polyethylene glycol. Thus, the compounds and their physiologically acceptable solvates may be formulated for administration.

Liquid formulations for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation by the patient.

The particles may be further coated. Suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Röhm Pharma, Darrnstadt, Germany), zein, shellac, and polysaccharides. Additionally, the coating material may contain conventional carriers such as plasticizers, pigments, colorants, glidants, stabilization agents, pore formers and surfactants.

III. Methods and Materials for Manufacture and Formulation of Nanoparticulate Vaccine Compositions A. Methods of Making Antigen-Encapsulated Nanoparticles Many different processes can be used to form the nanoparticles. If the process does not produce particles having a homogenous size range, then the particles can be separated using standard techniques such as sieving to produce a population of particles having the desired size range.

i. Solvent Evaporation

Methods for forming nanoparticles using solvent evaporation techniques are described in E. Mathiowitz, et al., *J. Scanning Microscopy,* 4:329 (1990); Beck, et al., *Fertil. Steril.,* 31:545 (1979); Beck, et al., *Am. J. Obstet. Gynecol.,* 135(3) (1979); Benita, et al., *J. Pharm. Sci.,* 73:1721 (1984); and U.S. Pat. No. 3,960,757 to Morishita, et al. The polymer is dissolved in a volatile organic solvent, such as methylene chloride. A substance to be incorporated optionally is added to the solution, and the mixture is suspended in an aqueous solution that contains a surface active agent such as poly (vinyl alcohol). Substances which can be incorporated in the nanoparticles include, but are not limited to, antigens, adjuvants, imaging agents, endosome-disrupting agents and contrast agents. The resulting emulsion is stirred until most of the organic solvent evaporated, leaving solid nano- and microparticles.

In a preferred embodiment, antigen-loaded, spherical PLGA nanoparticles with a mean diameter of 100-200 nm and protein loadings of up to 40% are produced by a modified version of this technique. In this method, 100 mg of PLGA is dissolved in 2 ml of methylene chloride in a short glass test tube (5.8 cm long, diameter 1.2 cm) overnight. To this solution, approximately 100-200 ul of the concentrated antigen solution is added and vortexed rapidly. This solution is added drop wise to 4 ml of an aqueous solution of 5% poly (vinyl alcohol) while vortexing. The emulsion formed is further sonicated three times for intervals of 10 seconds each at 38% amplitude (Tekmar Soni Disrupter model TM300, 40% duty cycle, microtip #4) to yield a homogeneous milky mixture. The single emulsion is poured into 100 ml of PVA 0.3%. The polymer/PVA dispersion is stirred on a magnetic stir plate for 3 hours at room temperature to allow for adequate solvent evaporation. Once solidified, the nanospheres are isolated by centrifugation (12000 rpm, 4° C., 10 minutes). The supernatant is discarded. Nanospheres are washed three times with deionized water (10 ml) to remove excess of PVA before they are frozen at −80° C. and then lyophilized for 48 hours. All parameters of this method are easily scaled to produce different batch sizes of nanoparticles.

This method is useful for relatively stable polymers like polyesters and polystyrene. However, labile polymers, such as polyanhydrides, may degrade during the fabrication process due to the presence of water. For these polymers, some of the following methods performed in completely anhydrous organic solvents are more useful.

ii. Hot Melt Microencapsulation

Microspheres can be formed from polymers such as polyesters and polyanhydrides using hot melt microencapsulation methods as described in Mathiowitz, et al., *Reactive Polymers,* 6:275 (1987). In this method, the use of polymers with molecular weights between 3-75,000 daltons is preferred. In this method, the polymer first is melted and then mixed with the solid particles of a substance to be incorporated that have been sieved to less than 50 microns. The mixture is suspended in a non-miscible solvent (like silicon oil), and, with continuous stirring, heated to above the melting point of the polymer, for example, 5° C. Once the emulsion is stabilized, it is cooled until the polymer particles solidify. The resulting microspheres are washed by decanting with petroleum ether to give a free-flowing powder. Microspheres with sizes between one to 1000 microns are obtained with this method.

iii. Solvent Extraction

This technique is primarily designed for polyanhydrides and is described, for example, in WO 93/21906 to Brown University Research Foundation. In this method, the substance to be incorporated is dispersed or dissolved in a solution of the selected polymer in a volatile organic solvent, such as methylene chloride. This mixture is suspended by stirring in an organic oil, such as silicon oil, to form an emulsion. Microspheres that range between 1-300 microns can be obtained by this procedure.

iv. Spray-Drying

Methods for forming microspheres using spray drying techniques are described in U.S. Pat. No. 6,620,617, to Mathiowitz et al. In this method, the polymer is dissolved in an organic solvent such as methylene chloride or in water. A known amount of an agent to be incorporated is suspended (insoluble agent) or co-dissolved (soluble agent) in the polymer solution. The solution or the dispersion then is spray-dried. Microspheres ranging between 0.1-10 microns are obtained.

v. Phase Inversion

Microspheres can be formed from polymers using a phase inversion method wherein a polymer is dissolved in a "good" solvent, fine particles of a substance to be incorporated, such as a drug, are mixed or dissolved in the polymer solution, and the mixture is poured into a strong non-solvent for the polymer, to spontaneously produce, under favorable conditions, polymeric microspheres, wherein the polymer is either coated with the particles or the particles are dispersed in the polymer. The method can be used to produce microparticles in a wide range of sizes, including, for example, about 100 nanometers to about 10 microns. Exemplary polymers which can be used include polyvinylphenol and polylactic acid. Substances which can be incorporated include, for example, imaging agents such as fluorescent dyes, or biologically active molecules such as proteins or nucleic acids. In the process, the polymer is dissolved in an organic solvent and then contacted with a non-solvent, which causes phase inversion of the dissolved polymer to form small spherical particles, with a narrow size distribution optionally incorporating an antigen or other substance.

B. Methods of Attaching Adaptor Elements to Nanoparticles

Adaptor elements may be conjugated to affinity tags prior to, or after their association with polymeric nanoparticles. In a preferred embodiment, the adaptor elements are fatty acids and the affinity tag is avidin/streptavidin. In a more preferred embodiment, palmitic acid is conjugated to avidin. In one method, avidin is dissolved at a concentration of 5 mg/ml in 37° C. prewarmed 2 ml solution of 2% deoxycholate in 1×PBS. To this solution, a 10 fold molar excess of NHS-Palmitic acid is added and the solution is stirred and sonicated in 37° C. water bath (Branson, 50 kHz freq.). The reaction is maintained at 37° C. for 24 hours after which excess palmitic acid is removed by dialysis against a 0.15% deoxycholate-PBS buffer prewarmed to 37° C. After three buffer changes, the avidin-palmitic acid conjugate is verified by reverse phase HPLC on a Prevail C18 column with a linear methanol gradient in 1×PBS as the mobile phase and UV detection at 280 nm. This method is easily adapted to conjugate avidin to any fatty acid of choice.

Avidin may be coupled to peptides and polymers by similar techniques. The chemistry involved in the coupling reaction will depend on the nature of available functional groups on the fatty acid, peptide or polymer. Methods for conjugating avidin to fatty acids, peptides and polymers are well known in the art. Methods for conjugating other affinity tags such as biotin, epitope tags (HA, FLAG, c-myc) and antibodies to fatty acids, peptides and polymers are well known in the art.

In a preferred embodiment, adaptor elements such as those described above, including fatty acids, hydrophobic or aliphatic peptides, and polymers, are conjugated onto the surface of nanoparticles at the emulsion stage of nanoparticle preparation. In a particularly preferred embodiment, the nanoparticles include PLGA and the adaptor elements include avidin-conjugated palmitic acid. In one method, dissolved PLGA solution is added to a 4 ml solution of 2 parts avidin-palmitic acid, 2 parts 5% PVA. A 50:50 mixture of protein-palmitic acid conjugates and 5% PVA has been found to yield optimal surface coverage of avidin groups on nanosized particles.

C. Methods of Attaching Functional Elements to Adaptor Elements

Functional elements can routinely be assembled onto adaptor elements incorporated onto the nanoparticle surface by conjugating the functional elements to affinity tags which are complementary to the affinity tags conjugated to the adaptor elements. Especially useful affinity tag pairs for use in coupling adaptor elements to functional elements are biotin-avidin and biotin-streptavidin. Affinity tag-conjugated functional elements are incubated with nanoparticles pre-coated with adaptor elements conjugated to complementary affinity tags under any appropriate buffer, salt and detergent conditions. For example, typical incubations may be performed at 4° C. for 2-4 hours, 37° C. for 20 minutes or room temperature for 1 hour. Incubations may be performed in phosphate buffered saline or other buffer compositions adjusted to a pH between 6.0 and 7.4. Incubation may occur with gentle shaking, rocking or rotation. Nanoparticles may then be washed with excess incubation buffer to remove unbound or non-specifically bound functional elements.

Functional elements may also be conjugated directly to adaptor elements in the absence of affinity tags, either prior to, or after their association with polymeric nanoparticles. Methods for conjugating functional elements such as peptides, polypeptides, polymers and antibodies to adaptor elements such as fatty acids, peptides and polymers are well known in the art. For example, fatty acids such as palmitic acid may be conjugated to the C-terminus of peptides, polypeptides and antibodies using a methodology similar to that described above for conjugation of palmitic acid to avidin.

IV. Methods of Using Nanoparticulate Vaccine Compositions

The nanoparticle vaccine compositions disclosed herein are useful for activating T cells in subjects for prophylactic and therapeutic applications. Activation of T cells by nanoparticle vaccine compositions increases their proliferation, cytokine production, differentiation, effector functions and/or survival. Methods for measuring these are well known to those in the art. The T cells activated by the nanoparticle vaccine compositions can be any cell which express the T cell receptor, including $\alpha/\beta$ and $\gamma/\delta$ T cell receptors. T-cells include all cells which express CD3, including T-cell subsets which also express CD4 and CD8. Other markers of T cell subsets include KLRG1, CD127, CD44 and combinations thereof. T-cells include both naive and memory cells and effector cells such as CTL. T-cells also include regulatory cells such as Th1, Tc1, Th2, Tc2, Th3, Treg, and Tr1 cells. T-cells also include NKT-cells and similar unique classes of the T-cell lineage. In preferred embodiments the T cells that are activated are $CD8^+$ T cells. As demonstrated in the examples below, the APCs disclosed herein preferentially activate and expand $CD8^+$ T cells when activated ex vivo.

A. Subjects to be Treated

In general, the compositions described herein are useful for treating a subject having or being predisposed to any disease or disorder to which the subject's immune system mounts an immune response. The compositions are useful as prophylactic vaccines, which confer resistance in a subject to subsequent exposure to infectious agents. The compositions are also useful as therapeutic vaccines, which can be used to initiate or enhance a subject's immune response to a pre-existing antigen, such as a tumor antigen in a subject with cancer, or a viral antigen in a subject infected with a virus. The compositions are also useful as desensitizing vaccines, which function to "tolerize" an individual to an environmental antigen, such as an allergen.

The ability to target these compositions to professional antigen-presenting cells such as dendritic cells, and the ability of these compositions to elicit T-cell mediated immune responses by causing cross-presentation of antigens makes these compositions especially useful for eliciting a cell-mediated response to a disease-related antigen in order to attack the disease. Thus, in a preferred embodiment, the type of disease to be treated or prevented is a malignant tumor or a chronic infectious disease caused by a bacterium, virus, protozoan, helminth, or other microbial pathogen that enters intracellularly and is attacked, i.e., by the cytotoxic T lymphocytes.

The desired outcome of a prophylactic, therapeutic or de-sensitized immune response may vary according to the disease, according to principles well known in the art. For example, an immune response against an infectious agent may completely prevent colonization and replication of an infectious agent, affecting "sterile immunity" and the absence of any disease symptoms. However, a vaccine against infectious agents may be considered effective if it reduces the number, severity or duration of symptoms; if it reduces the number of individuals in a population with symptoms; or reduces the transmission of an infectious agent. Similarly, immune responses against cancer, allergens or infectious agents may completely treat a disease, may alleviate symptoms, or may be one facet in an overall therapeutic intervention against a disease. For example, the stimulation of an immune response against a cancer may be coupled with surgical, chemotherapeutic, radiologic, hormonal and other immunologic approaches in order to affect treatment.

i. Subjects Infected with or Exposed to Infectious Agents

Subjects with or exposed to infectious agents can be treated therapeutically or prophylactically with nanoparticle vaccine compositions disclosed herein. Infectious agents include bacteria, viruses and parasites. In some instances, the subject can be treated prophylactically, such as when there may be a risk of developing disease from an infectious agent. An individual traveling to or living in an area of endemic infectious disease may be considered to be at risk and a candidate for prophylactic vaccination against the particular infectious agent. Preventative treatment can be applied to any number of diseases where there is a known relationship between the particular disease and a particular risk factor, such as geographical location or work environment.

ii. Subjects with or a Risk of Developing Malignant Tumors

In a mature animal, a balance usually is maintained between cell renewal and cell death in most organs and tissues. The various types of mature cells in the body have a given life span; as these cells die, new cells are generated by the proliferation and differentiation of various types of stem cells. Under normal circumstances, the production of new cells is so regulated that the numbers of any particular type of cell remain constant. Occasionally, though, cells arise that are no longer responsive to normal growth-control mechanisms. These cells give rise to clones of cells that can expand to a considerable size, producing a tumor or neoplasm. A tumor that is not capable of indefinite growth and does not invade the healthy surrounding tissue extensively is benign. A tumor that continues to grow and becomes progressively invasive is malignant. The term cancer refers specifically to a malignant tumor. In addition to uncontrolled growth, malignant tumors exhibit metastasis. In this process, small clusters of cancerous cells dislodge from a tumor, invade the blood or lymphatic vessels, and are carried to other tissues, where they continue to proliferate. In this way a primary tumor at one site can give rise to a secondary tumor at another site. The compositions and method described herein may be useful for treating subjects having malignant tumors.

Malignant tumors which may be treated are classified herein according to the embryonic origin of the tissue from which the tumor is derived. Carcinomas are tumors arising from endodermal or ectodermal tissues such as skin or the epithelial lining of internal organs and glands. A melanoma is a type of carcinoma of the skin for which this invention is particularly useful. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The types of cancer that can be treated in with the provided compositions and methods include, but are not limited to, the following: bladder, brain, breast, cervical, colo-rectal, esophageal, kidney, liver, lung, nasopharangeal, pancreatic, prostate, skin, stomach, uterine, and the like. Administration is not limited to the treatment of an existing tumor or infectious disease but can also be used to prevent or lower the risk of developing such diseases in an individual, i.e., for prophylactic use. Potential candidates for prophylactic vaccination include individuals with a high risk of developing cancer, i.e., with a personal or familial history of certain types of cancer.

iii. Subjects Exposed to Allergens

The vaccine compositions may be administered to subjects for the purpose of preventing and/or attenuating allergic reactions, such as allergic reactions which lead to anaphylaxis. Allergic reactions may be characterized by the $T_H2$ responses against an antigen leading to the presence of IgE antibodies. Stimulation of $T_H1$ immune responses and the production of IgG antibodies may alleviate allergic disease. Thus, the disclosed vaccine compositions may lead to the production of antibodies that prevent and/or attenuate allergic reactions in subjects exposed to allergens.

iv. Subjects with Immunosuppressed Conditions

Nanoparticle vaccines disclosed herein can be used for treatment of disease conditions characterized by immunosuppression, including, but not limited to, AIDS or AIDS-related complex, idiopathic immunosuppression, drug induced immunosuppression, other virally or environmentally-induced conditions, and certain congenital immune deficiencies. Nanoparticle vaccine compositions can also be employed to increase immune function that has been impaired by the use of radiotherapy of immunosuppressive drugs (e.g., certain chemotherapeutic agents), and therefore can be particularly useful when used in conjunction with such drugs or radiotherapy.

B. Methods of Administration

In general, methods of administering vaccines are well known in the art. Any acceptable method known to one of ordinary skill in the art may be used to administer a formulation to the subject. The administration may be localized (i.e., to a particular region, physiological system, tissue, organ, or cell type) or systemic. Vaccines can be administered by a number of routes including, but not limited to: oral, inhalation (nasal or pulmonary), intravenous, intraperitoneal, intramuscular, transdermal, subcutaneous, topical, sublingual, or rectal means. Injections can be e.g., intravenous, intradermal, subcutaneous, intramuscular, or intraperitoneal. In some embodiments, the injections can be given at multiple locations.

The nanoparticle vaccines disclosed herein are particularly suitable for enteral administration. The ability to target vaccine compositions to epithelial cells in the digestive tract greatly facilitates the ability of a vaccine to induce mucosal and systemic immunity when administered orally. Molecules, as described above, which protect the vaccine composition and its constituents from hydrolysis and degradation in low pH environments also enhance the efficacy of vaccines administered orally.

Administration of the formulations may be accomplished by any acceptable method which allows an effective amount of the vaccine to reach its target. The particular mode selected will depend upon factors such as the particular formulation, the severity of the state of the subject being treated, and the dosage required to induce an effective immune response. As generally used herein, an "effective amount" is that amount which is able to induce an immune response in the treated subject. The actual effective amounts of vaccine can vary according to the specific antigen or combination thereof being utilized, the particular composition formulated, the mode of administration, and the age, weight, condition of the individual being vaccinated, as well as the route of administration and the disease or disorder.

EXAMPLES

The present invention may be further understood by reference to the following non-limiting examples.

Example 1. Immune Cell-Specific Targeting of Nanoparticles

Materials and Methods:

Cells were adjusted to a concentration of $1\times10^7$ cells/ml in complete media. Plates were coated with various concentrations of anti-CDR antibodies according to established protocols. $2\times10^5$ cells were plated per well. Cells were treated with 20 nM complexes either loaded or unloaded with doxorubicin and incubated at 37° C., 5% $CO_2$. On day 3 T cell proliferation was analyzed with a colorimetric assay for quantification of cell proliferation and viability, WST-1®, according to manufacturer's protocol (Roche Diagnostics GmbH, Pennsburg, Germany).

Results:

Using avidin as an adaptor element coupled to fatty acid chains which insert readily into PLGA particles during fabrication, biotinylated antibodies and recombinant proteins that target different immune system cells were attached to the surface of the particles. These surface-modified particles interact specifically with cells and provide effective delivery of anti-proliferative drugs to intracellular compartments. For example, when modified with an antibody that recognizes T cells, Doxorubicin-loaded particles specifically reduced the proliferation of those cells (FIG. 1). Similar results were shown by targeting antigen-presenting cells using nanoparticulates presenting recombinant T cell receptors. These data demonstrate the utility of modular domains for directing nanoparticles to specific subsets of target cells. These data indicate that this approach can be extrapolated to target nanoparticles to other cell types, such as epithelial cells and dendritic cells by incorporating targeting modules onto nanoparticles specific to these cell types.

Example 2. Surface Modification of Nanoparticles with Immune Modulators Increases the Elicited Immune Response Materials and Methods:

Nanoparticles were prepared by a water-oil-water emulsion method using 50:50 Poly(DL-lactide-co-glycolide) from Lactel® with an inherent viscosity of 0.59 dL/g. PLGA was dissolved in methylene chloride. For loaded particles, aqueous solutions of 10 mg chicken egg albumin (ovalbumin, OVA-antigen) was emulsified into the dissolved polymer and sonicated for 30 seconds on ice (Tekmar, Model: TMX400). The resulting water in oil emulsion was subsequently added dropwise into the surfactant (5% Poly (vinyl alcohol) (PVA, Sigma-Aldrich®)) and sonicated again for 30 seconds. This was added to a stirring 0.3% PVA solution surfactant solution. After 3 hours particles were centrifuged at 12,000 RPM for 20 minutes and washed with DI water three times, frozen at −80° C., and lyophilized. LPS-coated particles were prepared with 20 mg/ml lipopolysaccharide (Sigma®, from *Escherichia coli*) in the surfactant. Nanoparticles were stored after lyophilization at −20° C. Nanospheres were characterized using scanning electron microscopy. Protein encapsulation was quantified by dissolving the particles in DMSO for 24 hr and performing a BCA Protein Assay (Pierce®).

Results:

Nanoparticulates encapsulating the model antigen, ovalbumin, were surface modified with lipopolysaccharide (LPS) and used to induce immunity in live animals against ovalbumin. LPS is a principal component of the cell wall of gram-negative bacteria and is a ligand for Toll like receptor 4, a major inducer of DC maturation and thus of T cell responsiveness (Reis e Sousa, *Semin. Immunol.*, 16(1):27-34 (2004); Bellou, et al., *Curr. Opin. Allergy Alin. Immunol.*, 3(6):487-94 (2003)). This biological property of LPS was exploited to engineer an immunogenic stimulus onto nanoparticles. LPS consists of a hydrophobic fatty acid chain conjugated to hydrophilic polysaccharide chains (Mayer, *Methods in Microbiology*, 18:157-207 (1985)). LPS is thus a similar composition to protein-fatty acid conjugates and serves as a model for incorporating protein-fatty acid conjugates onto PLGA nanoparticles for engineering high density protein display on the surface.

Figure 2A:
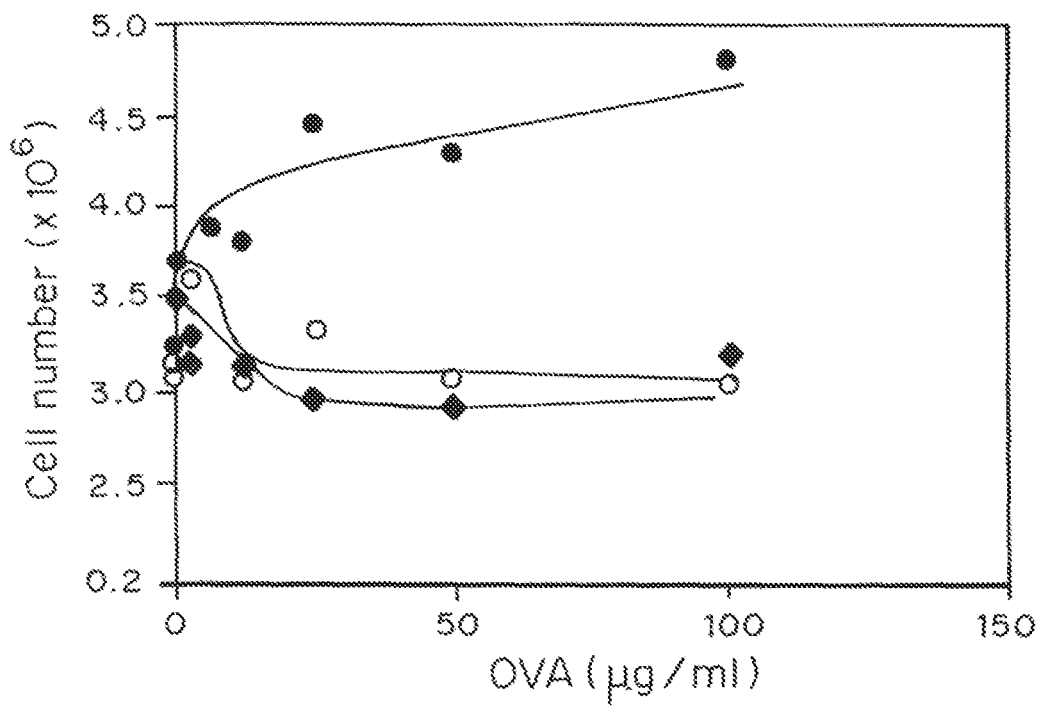
FIG. 2A is a graph showing that spleen cells obtained from mice three days after subcutaneous immunization with ovalbumin-encapsulated, LPS-modified, nanoparticles (-●-) proliferated (number of cells×$10^6$) in response to immobilized ovalbumin, thus demonstrating memory to the antigen. Controls are immobilized antigen (-○-) and blank nanoparticles (-◆-).
Figure 2B:
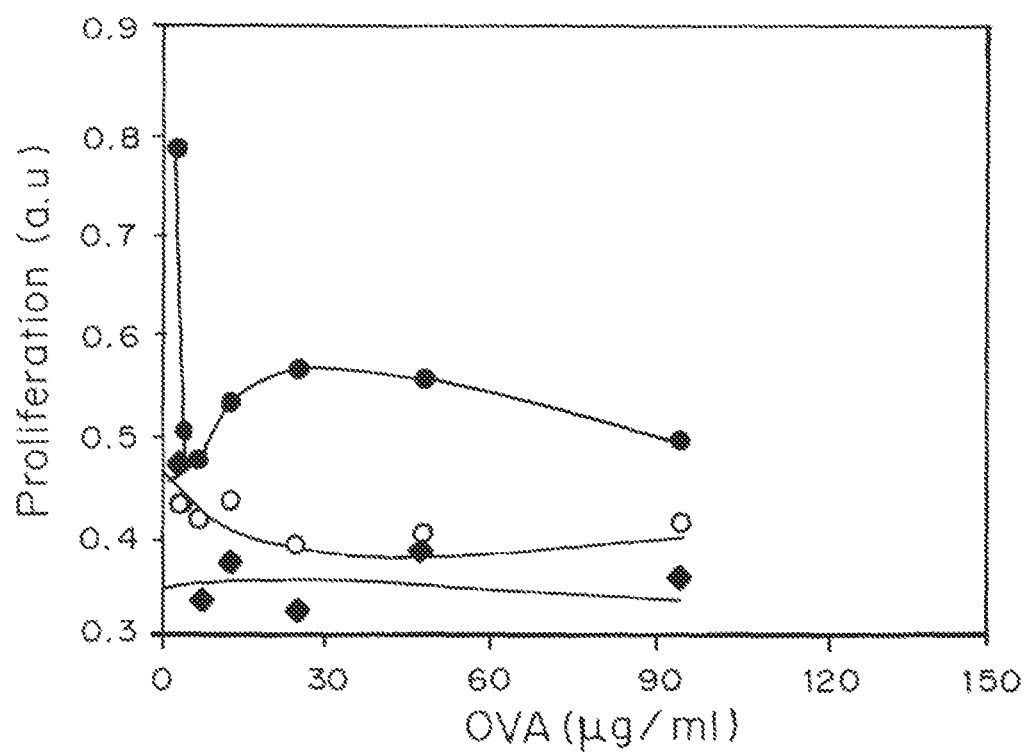
FIG. 2B is a graph showing that spleen cells obtained from mice following oral immunization with ovalbumin-encapsulated, LPS-modified, nanoparticles (-●-) proliferated (absorbance) in response to immobilized ovalbumin, demonstrating the efficacy of the particles in inducing immunity through oral administration. Controls are immobilized (-○-) antigen and blank nanoparticles (-◆-).

Only three days after immunization by subcutaneous injection, spleen cells isolated from injected mice showed a remarkable memory to the injected ovalbumin (FIG. 2A), as evidenced by proliferation of cells to immobilized antigen in a plate. This enhanced response was not observed with mice immunized with particles encapsulating the ovalbumin without LPS or with blank particles. Similar results were observed when animals were fed LPS-modified and unmodified particles (FIG. 2B), demonstrating the efficacy of this approach in inducing immunity by oral routes. This data demonstrates that nanoparticles encapsulating antigen can be made to be more effective vaccines by the proper choice and engineering of recognition elements into the surface. By derivatizing the nanoparticles with a simple immune modulator (LPS), the nanoparticles' ability to elicit an immune response was significantly enhanced. Addition of modules to enhance particle targeting, internalization, endosome escape, and extracellular protection will increase the degree to which these elements can further enhance their efficacy as vaccine vehicles.

Example 3. Endosome Disruption Enhances Antigen-Presentation by Dendritic Cells

Materials and Methods:

Particles prepared using the same preparation discussed in Example 2 with 100 μl of endoporter added to the emulsion at a concentration of 1 mg/ml.

Results:

Many pathogens make use of the acidic pH environment of endosomes and lysosomes to penetrate out from the confines of endocytic organelles into the cytosol. Some, in fact, do this by secreting pore-forming peptides that are low pH activated. Endoporter is a commercially available synthetic peptide that accomplishes this function (Summerton, *Ann. N.Y Acad. Sci.*, 1058:1-14 (2005)).

Figure 3:
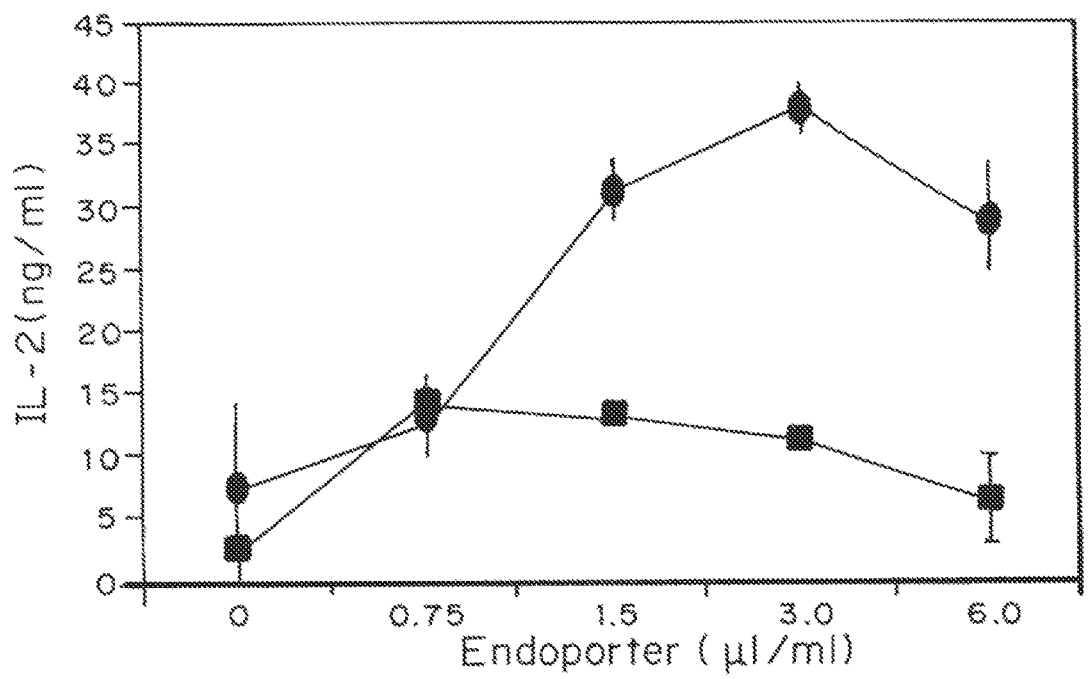
FIG. 3 is a graph showing release of IL-2 (ng/ml) by CD8 (OT-1) (-●-) and CD4 (OT-II) (-■-) positive T-cells as a function of the concentration of Endoporter (µl/ml) incubated with mouse bone marrow-derived dendritic cells. This graph demonstrates that inclusion of increasing concentrations of Endoporter enhanced cross presentation of antigen to MHC class I-restricted CD8 T-cells, while presentation to MHC class II-restricted CD4 T-cells was not diminished.
Figure 5:
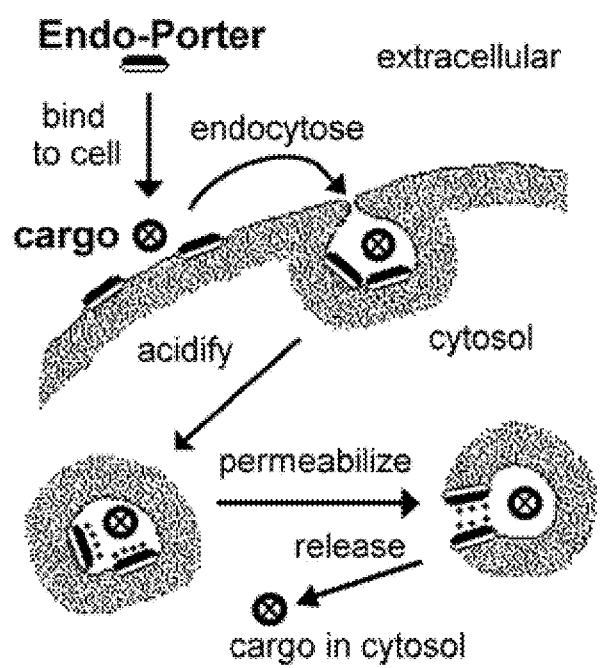
FIG. 5 is a diagram showing the mechanism of endosomal disruption following uptake of cargo by cells using endoporter as the exemplary endosomal targeting agent.

Mouse bone marrow-derived dendritic cells were incubated with soluble ovalbumin (0.1 mg/ml), a concentration that only inefficiently elicits antigen presentation to CD8 T cells. Inclusion of increasing concentrations of endoporter enhances cross presentation by 10-100-fold (depending on background) to the MHC class I-restricted, ovalbumin-specific CD8 T cell OT-I (as assayed by IL-2 release, (FIG. 3)). Importantly, presentation to MHC class II-restricted CD4 T cells (OT-II) was not diminished, even after endosome disruption (FIG. 3). Similar results were obtained when the ovalbumin was targeted to the dendritic cells by conjugation to anti-DEC-205 antibody. The results of these experiments demonstrate the efficacy of Endoporter in enhancing the presentation of exogenous antigens on MHC class I molecules to CD8 T cells, presumably by enhancing their penetration into the cytosol following endosomal disruption. Thus, endoporter significantly enhances a highly inefficient but essential aspect of antigen presentation required for effective immunity and vaccination to pathogens. The diagram in FIG. 5 demonstrates the mechanism for endosomal disruption by endoporter during cellular uptake of cargo.

Example 4. Co-Encapsulation of Positively Charged Macromolecules Small Molecules, or Oligonucleotides, Enhances Endosomal Disruption by Nanoparticles Materials and Methods:

Liposomal and polymeric particles, prepared with OVA and poly(amido amine) dendrimer generation 5 (PAMAM dendrimer G5), were incubated with bone-marrow derived dendritic cells (BMDCs) or bone marrow derived macrophages (BMDMs) for 24 hours. Endosomal disruption was measured indirectly through assessing the level of cross-presentation by the cells. Cross-presentation is a process where antigen escapes the endosomal compartment and is presented by the MHC in the cytosol. This presentation can be measured with an antibody (25.D16-PE). The amount of 25.D16-PE-positive cells represents the degree of cross-presentation mediated by endosomal disruption.

In another preparation, the PLGA nanoparticles were prepared carrying carbonyl cyanide 4-(trifluoromethoxy) phenylhydrazone (FCCP) via a dendrimer (G4) or cyclodextrin.

In another preparation, the monophosphoryl lipid A (MPLA) nanoparticles were prepared carrying G5 and/or CpG.

Figure 6:
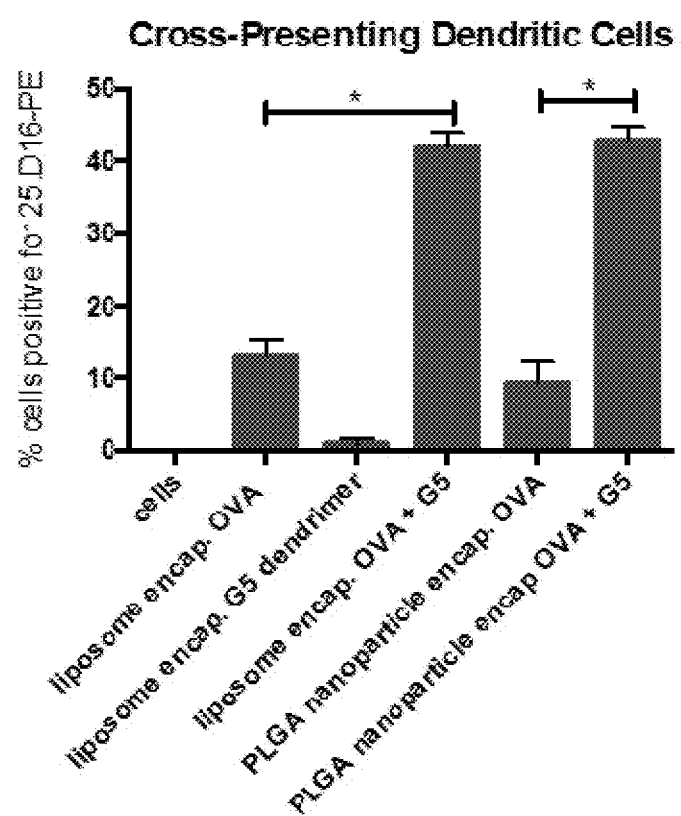
FIG. 6 is a bar graph showing endosomal disruption as percentage (%) of bone marrow derived dendritic cells positive for 26.D16-PE when incubated for 24 hours with PLGA or liposomal nanoparticles encapsulating a positively charged macromolecule dendrimer (G5) and the antigen ovalbumin.
Figure 7:
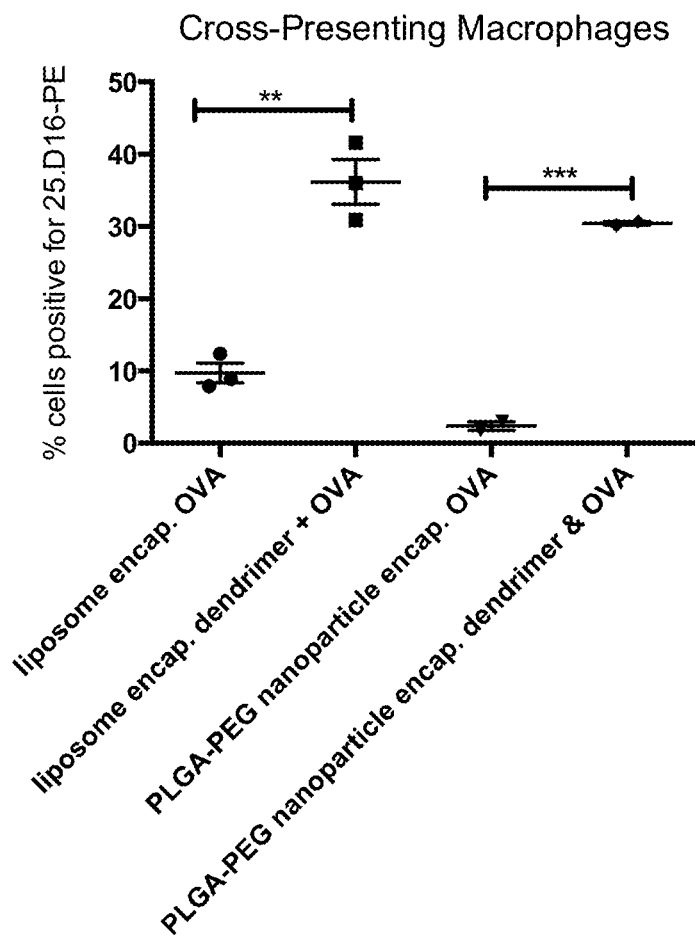
FIG. 7 is a dot plot showing endosomal disruption as percentage (%) of bone marrow derived macrophages positive for 26.D16-PE when incubated for 24 hours with PLGA-PEG or liposomal nanoparticles encapsulating a positively charged macromolecule dendrimer and the antigen ovalbumin.
Figure 8:
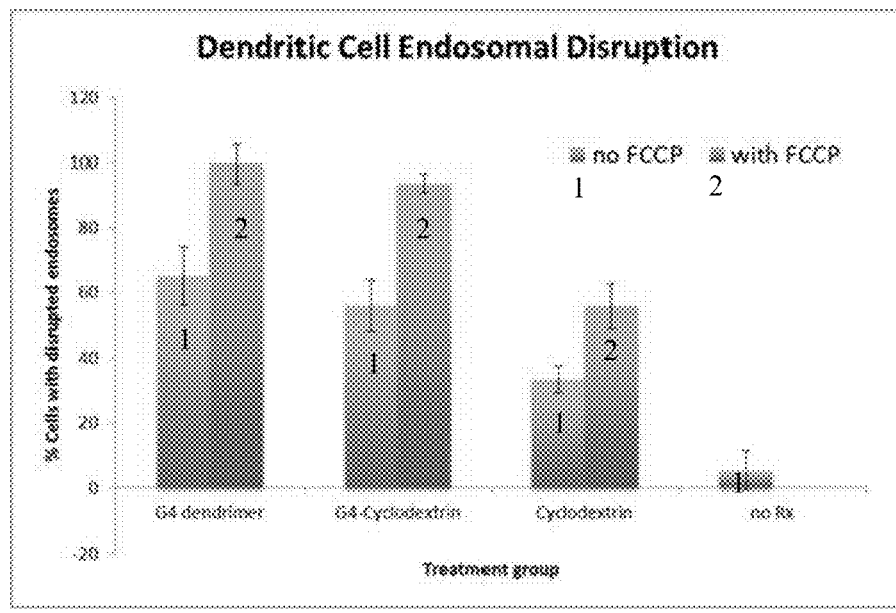
FIG. 8 is a bar graph showing percentage (%) of dendritic cells with disrupted endosomes when the cells are incubated with PLGA-dendrimer (G4) or PLGA-cyclodextrin nanoparticles without (1) or with (2) carbonyl cyanide 4-(trifluoromethoxy) phenylhydrazone (FCCP).

The prepared nanoparticles were tested for their ability to disrupt endosomes. Particles co-encapsulating the OVA peptide or GFP associated with the dendrimer were incubated at a concentration of 50 μg/ml with 1E5 BMDCs for 24 hours. Liposomal disruption was assessed both qualitatively via fluorescence microscopy of GFP in the cytosol or quantitatively by amount of OVA antigen presented via MHC Class I. Antigen presentation on Class I MHC takes place via cytosolic transport and OVA peptide/MHC Class I was detected specifically using the antibody 24D16-PE. FIGS. 6-7 show amount of antibody bound to the surface of DCs after particle internalization and compared to PLGA nanoparticles encapsulating the same antigen. FIG. 8 shows endosomal disruption assessed by quantitating cytosolic fluorescence in the presence and absence of a trifluoromethoxy phenylhydrazone (FCCP) a protonophore and uncoupler of oxidative phosphorylation in the mitochondria. FCCP is hosted in the dendrimer via a conjugated cyclodextrin molecule accommodating the hydrophobic FCCP molecule. The dendrimer/Cyclodextrin ratio is 1:5 and the figure shows that FCCP hosting can take place even without cyclodextrin attached since FCCP maybe associated with the dendrimer cavity itself.

It is therefore expected that FCCP would further disrupt the endosomal/lysosomal compartment resulting in increased fluorescence compared to dendrimer alone or the drug alone as shown in FIG. 7.

Results:

FIGS. 6 and 7 demonstrate that dendrimer (G5) encapsulation with antigen OVA increases cross-presentation in liposomal and polymeric nanoparticles (PLGA or PLGA-PEG nanoparticles) when co-incubated with mouse BMDCs or BMDMs.

FIG. 8 demonstrates that incorporation of FCCP significantly enhances the ability of PLGA-G4 or PLGA-G4-cyclodextrin nanoparticles to disrupt endosomes.

Figure 9:
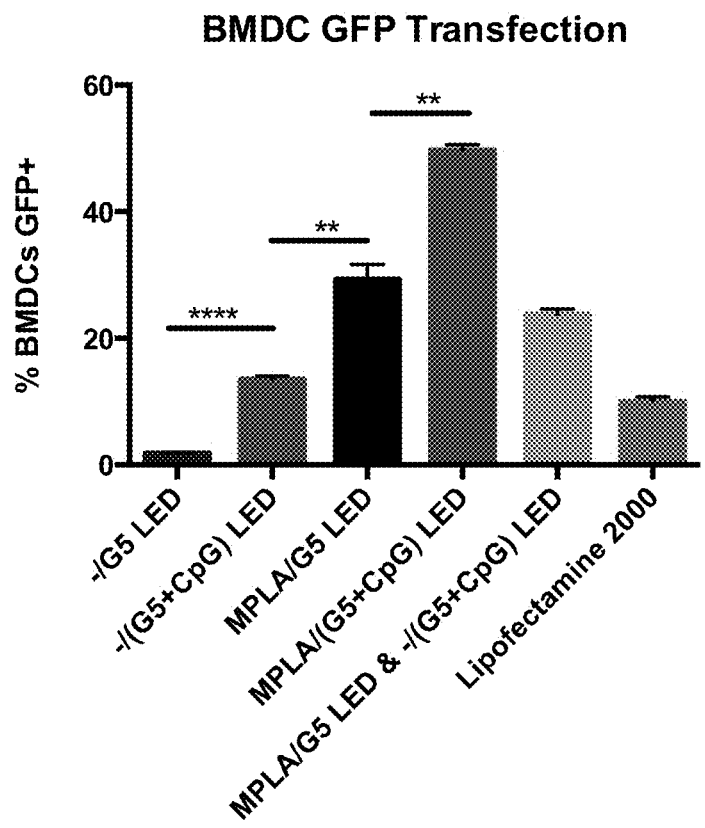
FIG. 9 is a bar graph showing percentage (%) of green fluorescent protein (GFP)-positive bone marrow derived dendritic cells transfected with monophosphoryl lipid A (MPLA) or liposomal nanoparticles co-encapsulating GFP, the dendrimer G5 and/or CpG DNA. LED stands for "Lipid Encapsulated Dendrimer". The different groups being: –/G5 LED is a Lipid Encapsulating Dendrimer of Generation 5 with no surface modification; (–/G5+CpG) LED is the same with co-encapsulated CpG associated with the encapsulated dendrimer; MPLA/G5 LED is the same with MPLA surface modified lipid and encapsulating G5 Dendrimer; MPLA/(G5+CpG) LED is MPLA surface modified lipid encapsulating CpG associated with the G5 Dendrimer; MPLA/G5 LED & –/(G5+CpG) LED are two particles with and without MPLA and unmodified particle encapsulating CpG; Lipofectamine is a gold standard for gene transfection.

FIG. 9 demonstrates that the highest percentage of transfection of bone marrow derived dendritic cells with GFP occurred when the cells were transfected with MPLA nanoparticles co-encapsulating GFP, the dendrimer G5 and CpG. The graph also describes the importance of having both TLR ligands associated with the same particle in that MPLA/G5 LED & −/(G5+CpG) LED is not as efficient in transfection compared to MPLA/(G5+CpG).

Example 5. Surface Modification of Nanoparticles with Protective Coatings Decreases Particle Degradation and Antigen Release Materials and Methods:

Particles were prepared as in Example 2. After lyophilization, biotin-elastin was prepared by biotinylation with NHS-LC-biotin (Pierce Chemicals). NHS-LC-biotin was incubated with 10 mg of particles (room temperature, 1 hour) at a concentration of 20 mg/ml. Following incubation, particles were washed by centrifugation 3× with deionized water and freeze-dried for further use. Controlled release studies were performed at the indicated pH.

Figure 4:
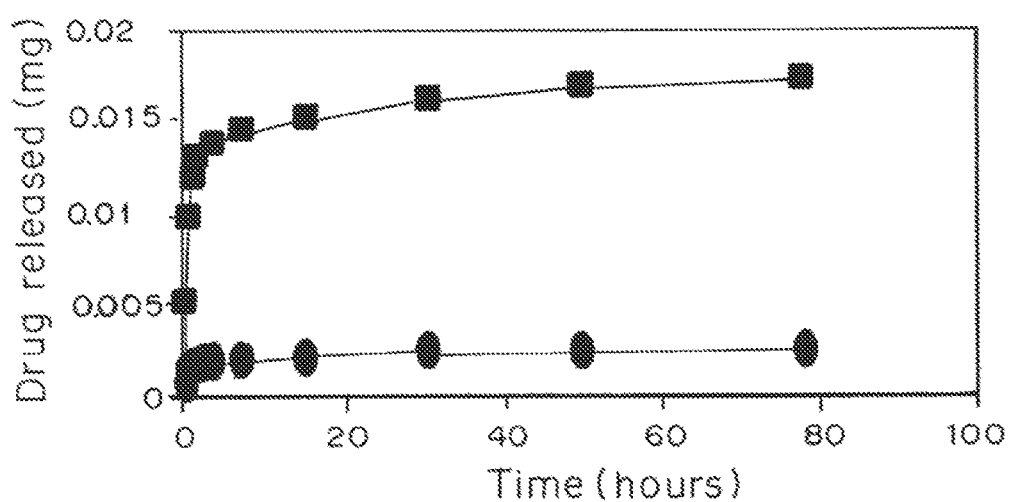
FIG. 4 is a graph demonstrating that nanoparticles conjugated to elastin (-●-) retain incorporated drug (mg) at low pH (pH=2) over time more readily than non-conjugated particles (-■-).

Results:

One advantage of antigen delivery using particles is the possibility of protecting the antigen against destruction in the GI tract following oral delivery. Elastin and poly(methacrylic) acid (PMAA) were conjugated to nanoparticles. As pH responsive polymers, both are in extended configurations at pH 7.4 and shrink rapidly (within seconds) upon exposure to lower pH environments (below pH 5 for elastin) and (below pH 5-6 for poly(methacrylic acid)). These data indicate that the addition of a pH responsive polypeptide or polymer to the surface of the nanoparticles can impart a protective effect to the particle affecting its degradation rate and antigen release (FIG. 4). The mechanism behind this protective ability may be due to the aggregation of the polymer at lower pH, restricting water entry and reducing the hydrolysis of the particle. Polymers such as PMAA in conjunction with poly(ethylene glycol) (PEG) have been used in past applications for enhancing the oral delivery of chemotherapeutic drugs, and thus there is good precedence for the use of these polymers as 'shielding' components in oral delivery (Blanchette and Peppas, *Ann. Biomed. Eng.*, 33(2):142-9 (2005); Blanchette and Peppas, *J. Biomed. Mater. Res. A*, 72(4):381-8 (2005)).

Example 6. Surface Modification of Nanoparticles Targets Different Dendritic Cell Subsets Materials and Methods:

Generation of Peptide-Loaded Nanoparticles (NPs)

PLGA NPs containing avidin on the surface were prepared using methods described by Park (Park et al., *J. Control. Release,* 156:109-115, 2011) and Fahmy (Fahmy et al., *Biomaterials,* 26:5727-5736, 2005). The prepared NPs included blank NP (no peptide), coumarin-labeled blank NP (NP-coumarin), NP-influenza-matrix peptide (FMP) (incorporating HLA A2.1 FMP sequence GILGFVFTL), NP-CEF (incorporating CEF pool peptide, pool of 32 peptides from EBV, CMV, and influenza virus, Anaspec), and NP-SOX2 (22 15-mer SOX2 peptides; Table 1). The amount of each peptide in the NPs was as follows: NP-FMP (9 µg/mg NP), NP-CEF (0.56 µg/mg NP), and NP-SOX2 (4.1 µg/mg NP).

TABLE 1

A list of SOX2 overlapping peptide sequences loaded in nanoparticles.

| Serial Number | SOX2 Peptide Sequence | SEQ ID NO. |
|---|---|---|
| 1 | LGAEWKLLSETEKR | SEQ ID NO: 1 |
| 2 | EWKLLSETEKRPFI | SEQ ID NO: 2 |
| 3 | LLSETEKRPFIDEAK | SEQ ID NO: 3 |
| 4 | TEKRPFIDEAKRLRA | SEQ ID NO: 4 |
| 5 | PFIDEAKRLRALHMK | SEQ ID NO: 5 |
| 6 | EAKRLRALHMKEH | SEQ ID NO: 6 |
| 7 | KRLRALHMKEHPDYK | SEQ ID NO: 7 |
| 8 | ALHMKEHPDYKYRPR | SEQ ID NO: 8 |
| 9 | KEHPDYKYRPRRKTK | SEQ ID NO: 9 |
| 10 | DYKYRPRRKTKTLMK | SEQ ID NO: 10 |
| 11 | RPRRKTKTLMKKDKY | SEQ ID NO: 11 |
| 12 | KTKTLMKKDKYTLPG | SEQ ID NO: 12 |
| 13 | LMKKDKYTLPGGLLA | SEQ ID NO: 13 |
| 14 | DKYTLPGGLLAPGG | SEQ ID NO: 14 |
| 15 | TLPGGLLAPGGNSMA | SEQ ID NO: 15 |
| 16 | GLLAPGGNSMASGVG | SEQ ID NO: 16 |
| 17 | PGGNSMASGVGVGAG | SEQ ID NO: 17 |
| 18 | SMASGVGVGAGLGAG | SEQ ID NO: 18 |
| 19 | GVGVGAGLGAGVNQR | SEQ ID NO: 19 |
| 20 | GAGLGAGVNQRMDSY | SEQ ID NO: 20 |
| 21 | GAGVNQRMDSYAHM | SEQ ID NO: 21 |
| 22 | VNQRMDSYAHMNGWS | SEQ ID NO: 22 |

TLR and/or antibody (Ab)-coated NPs were prepared by adding biotinylated LPS (InvivoGen), polyinosinic-polycytidylic acid [poly (I:C)] (InvivoGen), BDCA3 Ab (Miltenyi Biotec), or DC-SIGN Ab (Miltenyi Biotec) at the concentration of 5 µg Ab per milligram of NPs. The vials were gently rotated for 15 min. They were then centrifuged at 1200 rpm for 5 min to remove the supernatant and washed twice to remove any soluble ligand prior to use in experiments.

NP Targeting Experiments

Coumarin-labeled NPs were coated with either anti-BDCA3 or anti DC-SIGN antibody and co-cultured with peripheral blood mononuclear cells (PBMCs) for 30 min at 4° C.

Figure 10:
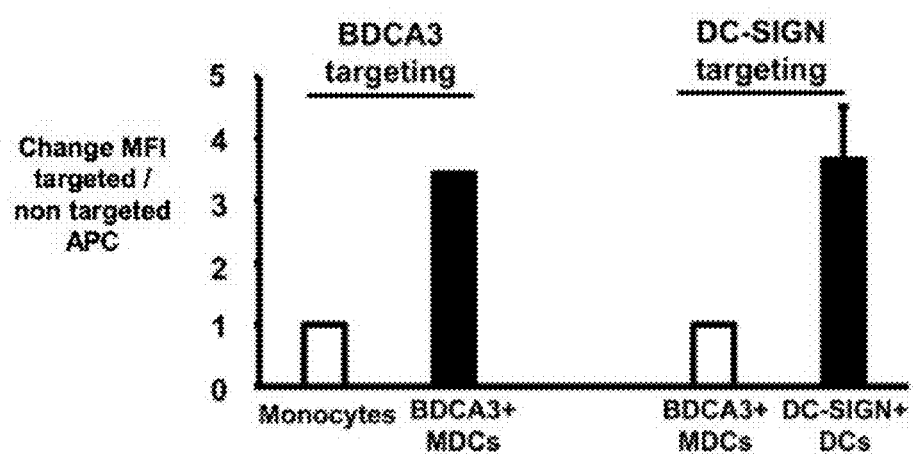
FIG. 10 is a bar graph showing change in MFI targeted/non targeted antigen presenting cells (APCs) when BDCA3+ and DC SIGN+DC subsets are targeted with nanoparticles surface modified with anti-BDCA3 and anti-DC-SIGN antibodies, respectively.
Figures 11A, 11B:
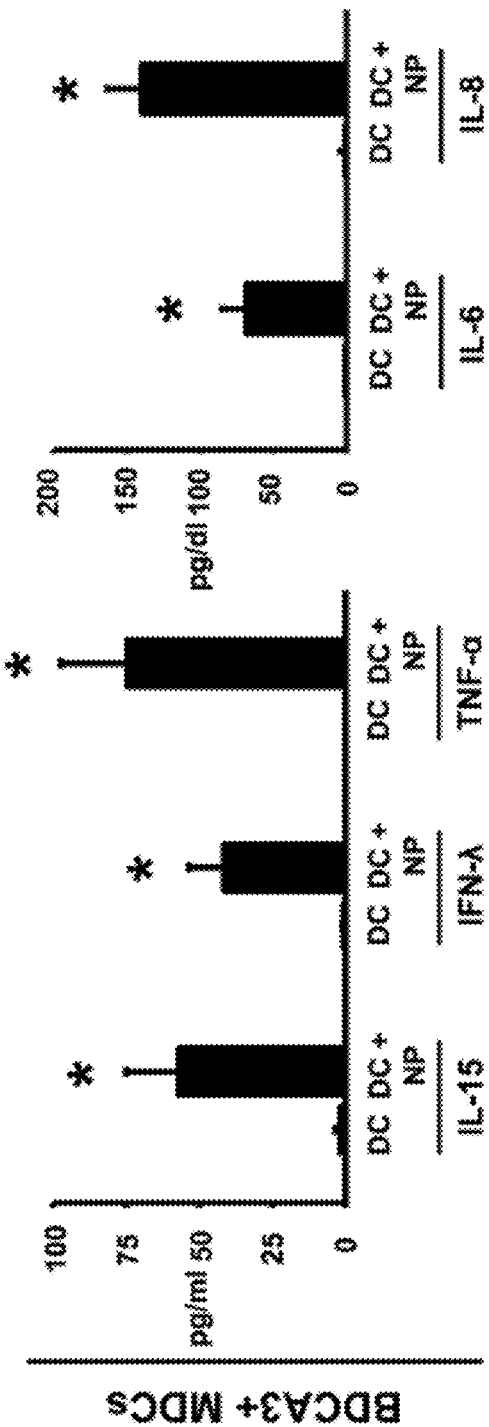

Results:

FIG. 10 demonstrates specific targeting of BDCA3+ and DC-SIGN+ dendritic cells with targeted NPs. The change in MFI of coumarin in targeted APCs over that in non-targeted APCs was greatest when BDCA3-targeted NPs were incubated with BDCA3+ myeloid dendritic cells (MDCs) and when DC-SIGN-targeted NPs were incubated with DC-SIGN+DCs.

Example 7. Targeting the Influenza Antigen to Dendritic Cells Potentiates the Immune Response Generation of Peptide-Loaded NPs PLGA NPs containing NP-influenza-matrix peptide (FMP) (incorporating HLA A2.1 FMP sequence GILGFVFTL) were prepared as described in Example 6.

Generation of DCs

Monocyte-derived DCs (Mo-DCs) were generated from PBMCs, as described by Dhodapkar (Dhodapkar et al., *Proc. Natl. Acad. Sci. USA,* 102:2910:2915, 2005). Briefly, CD14+ monocytes were isolated from PBMCs by immunomagnetic bead selection using CD14 beads following the manufacturer's protocol (Miltenyi Biotec). CD14+ cells were suspended in 1% healthy donor plasma in RPMI 1640 (Cellgro), supplemented with IL-4 (25 µg/ml; R&D Systems) and GM-CSF (20 ng/ml sargramostim (Leukine); Genzyme) on days 0, 2, and 4 of culture. Immature Mo-DCs were harvested on days 5-6 and used for the experiments described below. The CD14− fraction of PBMCs was cultured in the presence of 5% pooled human serum (Labquip) in RPMI 1640. BDCA3+ MDCs were isolated from the PBMCs using BDCA3 MACS beads (Miltenyi Biotec).

NP Uptake Experiments

The effects of NPs on isolated BDCA3+ MDCs and DC-SIGN+ Mo-DCs were studied by incubating the cells overnight with NP-FMP (peptide concentration 0.05 µg/ml) at 37° C. BDCA3+ MDCs isolated from healthy donor buffy coats or DC-SIGN+ Mo-DC were loaded with NP-FMP at 37° C. and supernatants were collected after 24 h. Cytokines were quantified using VeriPlex Human Cytokine ELISA (PBL IFN source) and data were analyzed by Q-View 2.160 software (Quansys Biosciences). BDCA3+ MDCs and DC-SIGN DCs incubated alone were used as negative controls.

Results:

FIGS. 11A-11D demonstrate that targeting the influenza antigen (FMP) to BDCA3+ or DC-SIGN+DC subsets potentiates the immune response. The graph shows mean cytokine expression levels (IL-15, IFN-$\lambda$ and TNF-$\alpha$ in pg/ml, and IL-6 and IL-8 in pg/dl, ±SEM) per 30,000 APCs for cells obtained from three different healthy donors. *$p<0.05$.

Example 8. Delivery of Combination of Peptides by Dendritic Cells Stimulates a Specific and Multivalent T Cell Response Materials and Methods Generation of CEF Peptide-Loaded NPs Nanoparticles loaded with CEF combination of 32 peptides were prepared as described in Example 6.

Antigen-Specific T Cell Stimulation

Day 6 immature Mo-DCs or freshly isolated BDCA3+ MDCs were loaded with either blank NPs or NPs encapsulated with CEF pool peptide (NP-CEF) for 1 h. After overnight culture in 1% plasma, NP-loaded DCs were used to stimulate autologous T cells at a DC/T cell ratio of 1:30 in the presence of IL-2 (10 μg/ml at days 4 and 7; Chiron). After 10-12 days in culture, flow cytometry was performed to detect the presence of antigen-specific T cells intracellular cytokine secretion assay for IFN-γ, with the peptides used for initial T cell stimulation in the presence of anti-CD28 and anti-CD49D (1 μg/ml).

Figure 12:
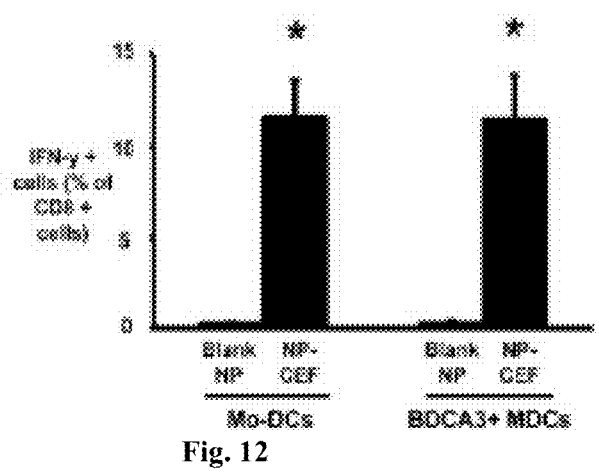
FIG. 12 is a bar graph showing mean percentage (%, ±SEM) of CD8+ cells producing IFN-γ when stimulated by Mo-DCs or BDCA3+ MDCs loaded with either blank NP or NP-CEF.

Results:

BDCA3+ MDCs were able to stimulate Ag-specific IFN-γ-secreting T cells in response to NP-CEF. Importantly, the elicited immune response included reactivities against multiple peptides within the mix. Induction of IFN-γ production by CD8 lymphocytes from a healthy donor in response to antigen-specific stimulation by NP-CEF-loaded autologous BDCA3+ MDCs and absence of stimulation by autologous BDCA3+ MDCs loaded with blank NP FIG. 12 demonstrates the mean percentage (%, ±SEM) of CD8 cells producing IFN-γ when stimulated by Mo-DCs (n=8) or BDCA3+ MDCs (n=3) loaded with either blank NP or NP-CEF. *p=6×10$^{-4}$ (blank NP versus NP-CEF for Mo-DCs) and p=4.9×10$^{-2}$ (blank NP versus NP-CEF for BDCA3+MDCs).

The multivalent nature of the CD8+ T cell response following stimulation by Mo-DCs or BDCA3+ MDCs loaded with either blank NP or NP-CEF was confirmed when the CD8+ T cells were re-stimulated with individual peptide components (Pep1-Pep18; described in Table 2) of the CEF peptide pool. Blank NP and NP-CEF restimulated with CEF pool peptide were used as negative and positive controls, respectively.

TABLE 2

A list of combinations of CEF peptides from EBV, HCMV and influenza.

| Peptide | HLA Allele | Virus | Protein & Region | Peptide Sequence | SEQ ID NO. |
|---|---|---|---|---|---|
| Pep 1 | A1 | INFLUENZA A | PB1 (591-599) | VSDGGPNLY | SEQ ID NO: 23 |
| Pep 2 | A2 | EBV | BMLF1 (259-267) | GLCTLVAML | SEQ ID NO: 24 |
| Pep 3 | A2 | INFLUENZA A | MATRIX 1 (58-66) | GILGFVFTL | SEQ ID NO: 25 |
| Pep 4 | A3 | INFLUENZA A | NP (265-273) | ILRGSVAHK | SEQ ID NO: 26 |
| Pep 5 | A3 | EBV | BRLF1 (148-156) | RVRAYTYSK | SEQ ID NO: 27 |
| Pep 6 | A3 | EBV | EBNA 3A (603-611) | RLRAEAQVK | SEQ ID NO: 28 |
| Pep 7 | A11 | EBV | EBNA 3B (416-424) | IVTDFSVIK | SEQ ID NO: 29 |
| Pep 8 | A11 | EBV | BRLF1 (134-143) | ATIGTAMYK | SEQ ID NO: 30 |
| Pep 9 | A24 | EBV | BRLF1 (28-37) | DYCNVLNKEF | SEQ ID NO: 31 |
| Pep 10 | A68 | INFLUENZA A | NP (91-99) | KTGGPIYKR | SEQ ID NO: 32 |
| Pep 11 | B7 | EBV | EBNA 3A (379-387) | RPPIFIRRL | SEQ ID NO: 33 |
| Pep 12 | B8 | EBV | EBNA 3A (158-166) | QAKWRLQTL | SEQ ID NO: 34 |
| Pep 13 | B8 | EBV | EBNA 3A (325-333) | FLRGRAYGL | SEQ ID NO: 35 |
| Pep 14 | B8 | EBV | BZLF1 (190-197) | RAKFKQLL | SEQ ID NO: 36 |
| Pep 15 | B27 | EBV | EBNA 3C (258-266) | RRIYDLIEL | SEQ ID NO: 37 |
| Pep 16 | B27 | INFLUENZA A | NP (383-391) | SRYWAIRTR | SEQ ID NO: 38 |
| Pep 17 | B35 | EBV | EBNA 3A (458-466) | YPLHEQHGM | SEQ ID NO: 39 |
| Pep 18 | B44 | HCMV | Pp65 (512-521) | EFFWDANDIY | SEQ ID NO: 40 |

Example 9. Delivery of Combinations of Tumor Antigen Peptides of SOX2 to Dendritic Cells Leads to Stimulation of Antigen-Specific CD4 as Well as CD8 T Cells Materials and Methods:

Generation of CEF Peptide-Loaded NPs

Nanoparticles loaded with tumor antigen peptides of SOX2 were prepared as described in Example 6.

Antigen-Specific T Cell Stimulation

Day 6 immature Mo-DCs were loaded with either blank NPs or NPs encapsulated with SOX2 pool peptide (NP-SOX2, Table 1) for 4 hours. After overnight culture in 1% plasma, NP-loaded DCs were used to stimulate autologous T cells at a DC/T cell ratio of 1:30 in the presence of IL-2 (10 μg/ml at days 4 and 7; Chiron). After 10-12 days in culture, flow cytometry was performed by intracellular cytokine secretion assay for IFN-γ, with the peptides used for initial T cell stimulation in the presence of anti-CD28 and anti-CD49D (1 μg/ml).

T cells were restimulated with NP-SOX2 loaded DCs on days 7 and 14 in the presence of IL-2 (10 μg/ml) as well as IL-7 and IL-15 (both at 5 μg/ml; R&D Systems). For some experiments, DCs were matured overnight with LPS (50 ng/ml; Sigma-Aldrich) or poly(I:C) (25 μg/ml; Sigma-Aldrich) or cytokine mixture [IL-6 (0.01 μg/ml; R&D Systems), IL-1β (0.01 μg/ml; R&D Systems), TNF-α (0.01 μg/ml; R&D Systems), and PGE2 (1 μg/ml, Sigma-Aldrich)] after loading with NPs.

Results:

NP-SOX2-loaded autologous DCs were used to stimulate T cells because SOX2 peptides are 15 aa long and require active processing for antigen presentation. DCs loaded with NP-SOX2 were able to stimulate both SOX2-specific CD4 and CD8+ T cells in culture. Taken together these data demonstrate that both BDCA3+ and Mo-DC-SIGN+NP-loaded DCs are equally effective at generating antigen-specific human T cells in culture, including against complex peptide mixtures from viral and tumor antigens across multiple MHC molecules.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims. Those skilled in the art will recognize, or be able to ascertain using no more than routine experimentation, many equivalents to the specific embodiments of the invention described herein. Such equivalents are intended to be encompassed by the following claims.

We claim:

1. A vaccine composition comprising polymeric nanoparticles for inducing an immune response, wherein the polymeric nanoparticles are taken up by antigen presenting cells and comprise:
   one or more antigens; and
   targeting molecules associated with the same or different nanoparticles, the targeting molecules targeting at least two different subsets of antigen presenting cells.

2. The composition of claim 1 wherein the antigen is selected from the group consisting of viral, bacterial, parasitic, allergen, toxoid, tumor-specific and tumor-associated antigens.

3. The composition of claim 1 wherein the nanoparticles further comprise a functional element comprising pH-sensitive or non-pH-sensitive molecules that protect the nanoparticles from hydrolysis and degradation in low pH environments.

4. The composition of claim 1 further comprising an adjuvant, an immune modulator, a contrast agent or other marker, or a combination thereof.

5. The composition of claim 4 wherein the adjuvant or immune modulator is selected from the group consisting of a cytokine, an interleukin, an interferon, a macrophage colony stimulating factor, a tumor necrosis factor, and a member of the B7 family of co-stimulatory molecules.

6. The composition of claim 4 wherein the adjuvant or immune modulator is a glycolipid that is a stimulator of natural killer T cell-mediated immune responses.

7. The composition of claim 6 wherein the glycolipid is α-galactosylceramide.

8. The composition of claim 1 wherein one or more of the targeting molecules target the nanoparticles to a cell-type specific receptor.

9. The composition of claim 8 wherein the targeting molecules are selected from the group consisting of monoclonal or polyclonal antibodies, ligands that bind to a receptor on dendritic cells, ligands that bind to a receptor on epithelial cells, and combinations thereof.

10. The composition of claim 1 further comprising molecules that protect the composition from hydrolysis and degradation in low-pH environments selected from the group consisting of gelatin, albumin, poly(acrylic acid), poly(methyl methacrylic acid) poly(N-alkyl acrylamides), elastin, poly(methacrylic acid), and poly(ethylene) glycol.

11. The composition of claim 1, wherein the nanoparticles further comprise a contrast agent, a fluorescent tag, or a radionuclide.

12. The composition of claim 1 further comprising pharmaceutically acceptable excipients suitable for enteral administration.

13. The composition of claim 1 further comprising pharmaceutically acceptable excipients suitable for parenteral administration.

14. The composition of claim 1 wherein the targeting molecules target two or more of the molecules in the group consisting of DEC-205, DC-SIGN, 33D1, SIGLEC-H, DCIR, CD11c, heat shock protein receptors, scavenger receptors, mannose-specific lectin (mannose receptor), IgG Fc receptors, and toll-like receptors (TLRs).

15. The composition of claim 1 wherein the at least two subsets of targeting molecules are associated with different nanoparticles, wherein one targeting molecule targets DC-SIGN+ dendritic cells.

16. The composition of claim 1 wherein the nanoparticles further comprise an endosome-disrupting agent which is not poly(lactic-co-glycolic acid) (PLGA).

17. The composition of claim 16 wherein the endosome-disrupting agent is a small molecule drug, peptide, polypeptide, or synthetic agent.

18. The composition of claim 1 wherein the nanoparticles further comprise one or more functional elements selected from the group consisting of adjuvants, immune potentiators, molecular recognition factors, transport mediation elements, and intracellular uptake mediators.

19. The composition of claim 1 wherein the nanoparticles further comprise an endosome-disrupting agent which is not poly(lactic-co-glycolic acid) (PLGA), one or more functional elements selected from the group consisting of adjuvants, immune potentiators, molecular recognition factors, transport mediation elements, and intracellular uptake mediators, or a combination thereof,
wherein the antigen, one or more of the targeting molecules, one or more of the functional elements, or a combination thereof is bound to the nanoparticles by an adaptor element.

20. The composition of claim 19 wherein the adaptor element is coupled directly to the antigen, the targeting molecules, the functional element, the endosome-disrupting agent, or a combination thereof by covalent bonds.

21. The composition of claim 19 wherein the adaptor element is conjugated to an affinity tag.

22. The composition of claim 21 wherein the adaptor element is coupled to the antigen, the targeting molecules, the endosomal-disrupting agent, the functional element, or a combination thereof by the non-covalent interaction of the affinity tag conjugated to the adaptor element and a complementary affinity tag conjugated to the antigen, the targeting molecules, the endosomal-disrupting agent, the functional elements, or the combination thereof.

23. The composition of claim 21 wherein the affinity tag comprises avidin or streptavidin.

24. The composition of claim 19 wherein the adaptor element comprises one or more of fatty acids, hydrophobic or amphipathic peptides, and hydrophobic polymers.

25. A method for inducing an immune response to an antigen comprising administering to a subject in need thereof an effective amount of a vaccine composition comprising polymeric nanoparticles for inducing the immune response, wherein the polymeric nanoparticles are taken up by antigen presenting cells and comprise:
one or more antigens; and
targeting molecules associated with the same or different nanoparticles, the targeting molecules targeting at least two different subsets of antigen presenting cells the composition of claim 1.

26. The method of claim 25 wherein the composition is administered enterally.

27. The method of claim 25 wherein the composition is administered parenterally.

28. The method of claim 25 wherein the vaccine composition comprises two or more antigens and is in an effective amount to induce immune responses to the two or more antigens.

* * * * *